(12) United States Patent
Paul, Jr. et al.

(10) Patent No.: US 10,111,666 B2
(45) Date of Patent: Oct. 30, 2018

(54) DISSOLVABLE SLEEVE CONFIGURATIONS TO AID GRAFT DEPLOYMENT

(71) Applicant: Cook Medical Technologies LLC, Bloomington, IN (US)

(72) Inventors: Ram Paul, Jr., Bloomington, IN (US); Christopher D. Bosel, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 200 days.

(21) Appl. No.: 14/919,086

(22) Filed: Oct. 21, 2015

(65) Prior Publication Data

US 2016/0120548 A1 May 5, 2016

Related U.S. Application Data

(60) Provisional application No. 62/126,065, filed on Feb. 27, 2015, provisional application No. 62/075,592, filed on Nov. 5, 2014.

(51) Int. Cl.
*A61F 2/06* (2013.01)
*A61B 17/11* (2006.01)
*A61F 2/82* (2013.01)
*A61F 2/848* (2013.01)

(52) U.S. Cl.
CPC .............. *A61B 17/11* (2013.01); *A61F 2/064* (2013.01); *A61F 2/82* (2013.01);
(Continued)

(58) Field of Classification Search
CPC ............ A61B 17/11; A61B 2017/1107; A61B 2017/1132; A61B 17/1114; A61B 2017/1103; A61B 2017/111; A61B 2017/1135; A61B 2017/1139; A61B 2017/1142; A61F 2/064; A61F 2002/8483; A61F 2250/003; A61F 2250/0031;
(Continued)

(56) References Cited

U.S. PATENT DOCUMENTS 6,827,731 B2* 12/2004 Armstrong ................ A61F 2/95
623/1.12
2007/0027526 A1* 2/2007 Demetriades ............ A61F 2/07
623/1.13
(Continued)

FOREIGN PATENT DOCUMENTS

WO    WO 02/076340 A2    10/2002

OTHER PUBLICATIONS

International Search Report for PCT/US2015/056629, dated Jan. 13, 2016, 13 pages.
(Continued)

*Primary Examiner* — Katrina Stransky
*Assistant Examiner* — Kankindi Rwego
(74) *Attorney, Agent, or Firm* — Brinks Gilson & Lione

(57) ABSTRACT

A prosthesis including a self-expanding stent, a graft body, and one or more sleeves is disclosed, in addition to methods of treatment using the prosthesis. The proximal and distal ends of the prosthesis may include one or more sleeves and one or more barbs. The sleeves may be removable or dissolvable, for example, upon exposure to an activating agent. The prosthesis may be used to treat lacerated vessels and transected vessels.

22 Claims, 9 Drawing Sheets

(52) U.S. Cl.
CPC .............. *A61B 2017/1107* (2013.01); *A61B 2017/1132* (2013.01); *A61F 2002/8483* (2013.01); *A61F 2250/003* (2013.01); *A61F 2250/0031* (2013.01); *A61F 2250/0036* (2013.01)

(58) Field of Classification Search
CPC ...... A61F 2250/0036; A61F 2/06; A61F 2/82; A61F 2/95; A61F 2/954; A61F 2/958; A61F 2/962; A61F 2/966; A61F 2/97
USPC ................................................. 623/1, 1.13
See application file for complete search history.

(56) References Cited

U.S. PATENT DOCUMENTS

| | | | |
|---|---|---|---|
| 2012/0035706 A1 | 2/2012 | Paul, Jr. et al. | |
| 2012/0123511 A1* | 5/2012 | Brown | A61F 2/064 623/1.11 |
| 2012/0271402 A1 | 10/2012 | Sargent, Jr. | |
| 2014/0324155 A1 | 10/2014 | Paul | |
| 2015/0005872 A1* | 1/2015 | Theobald | A61F 2/06 623/1.15 |

OTHER PUBLICATIONS

International Search Report and Written Opinion for corresponding International Application No. PCT/US2015/056629, dated Jan. 13, 2016 (13 pages).

* cited by examiner

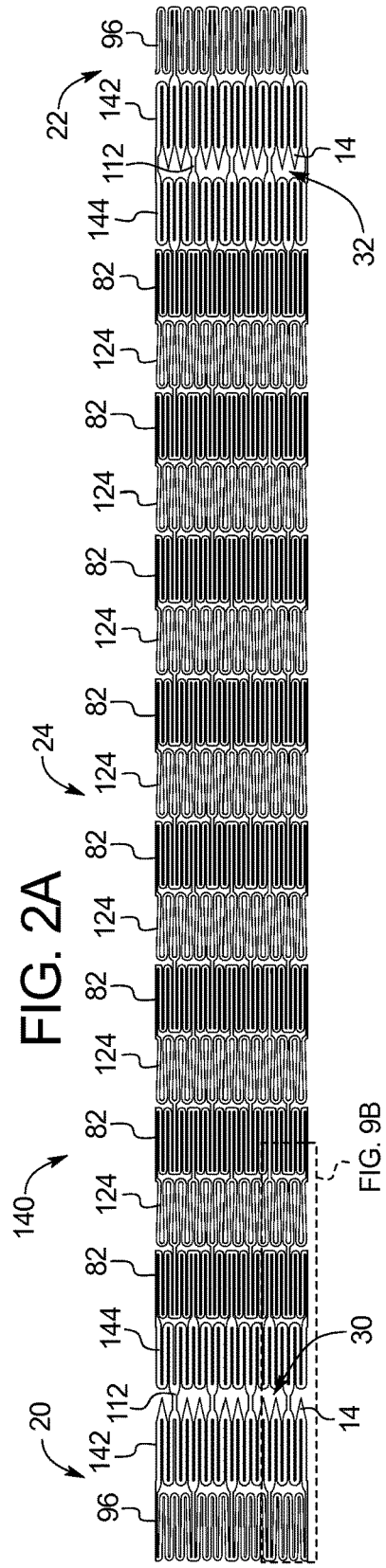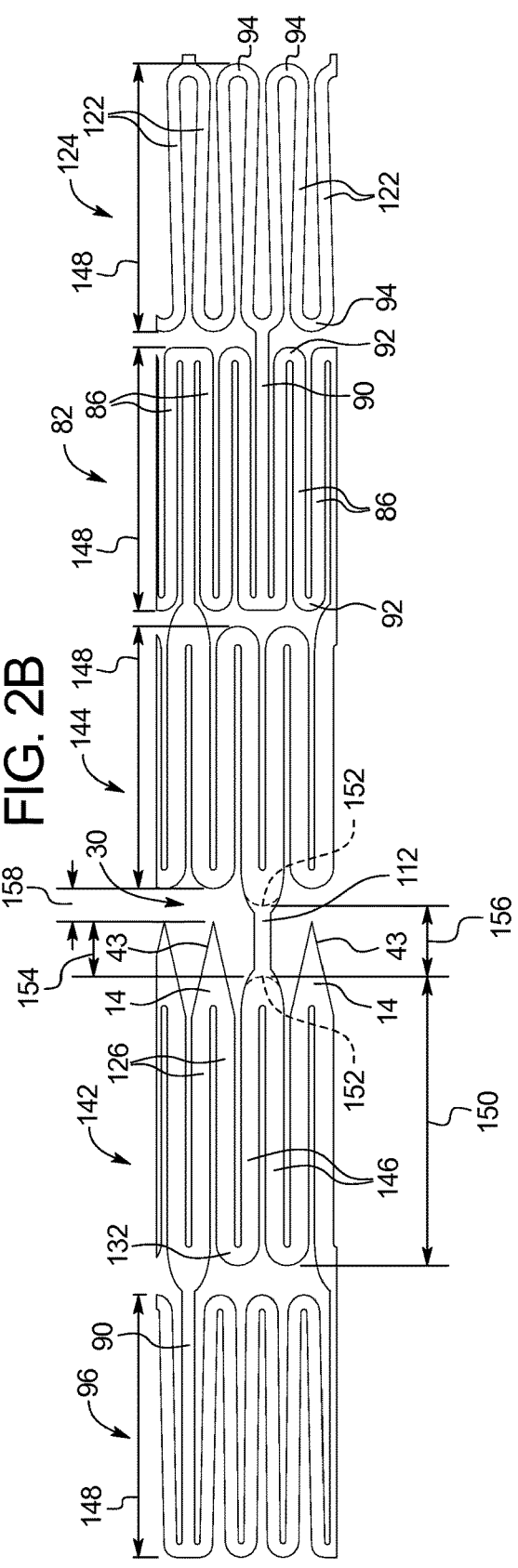

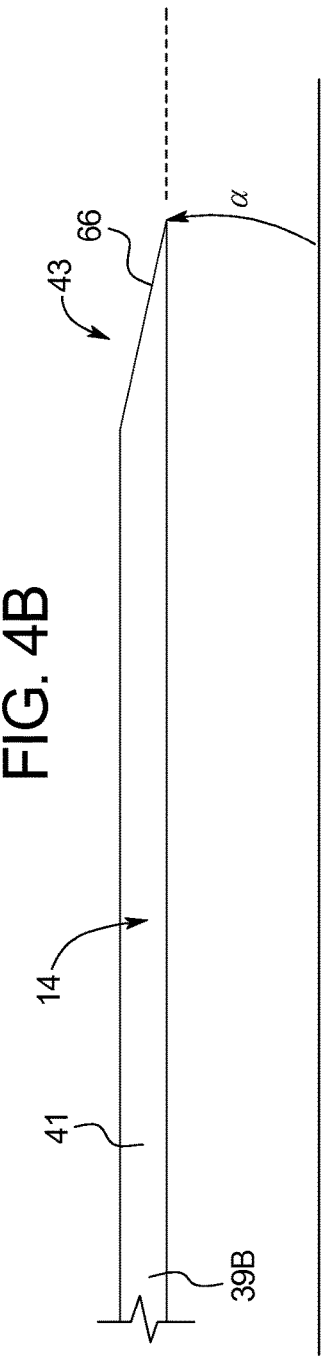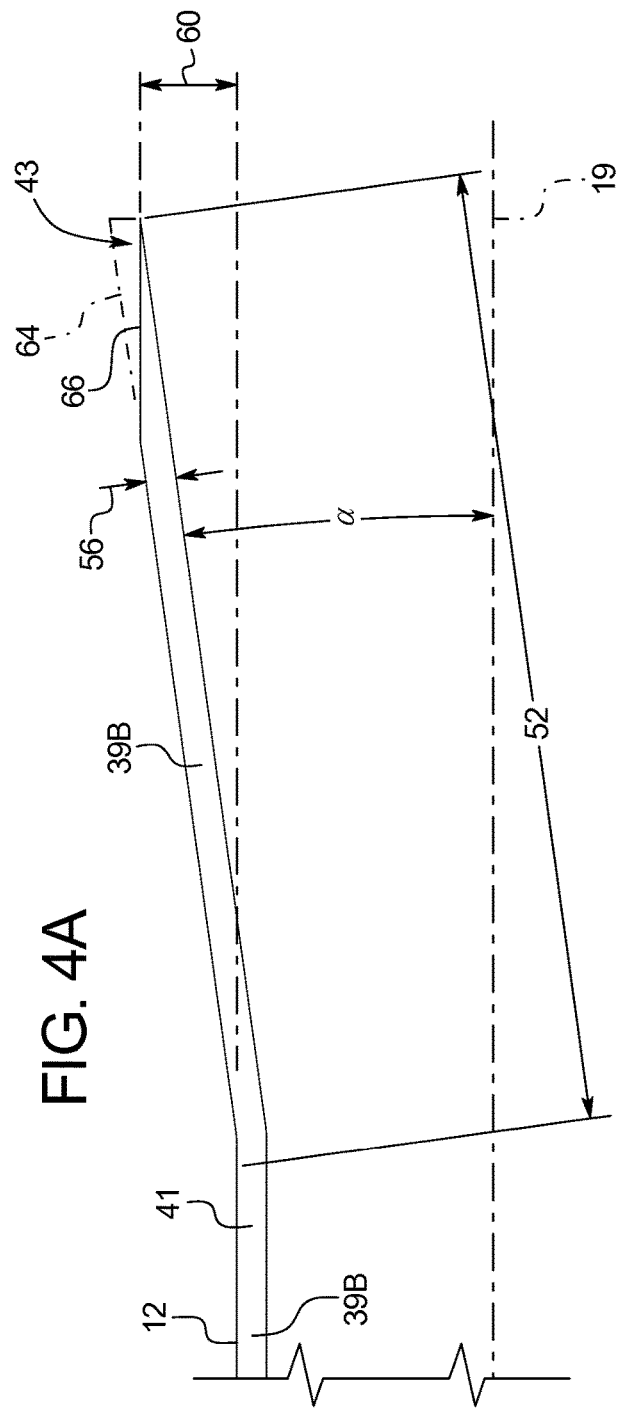

DISSOLVABLE SLEEVE CONFIGURATIONS TO AID GRAFT DEPLOYMENT

CROSS-REFERENCE TO RELATED APPLICATIONS

The present application claims the benefit of U.S. Provisional Patent Application No. 62/075,592 filed Nov. 5, 2014, and U.S. Provisional Patent Application No. 62/126,065 filed Feb. 27, 2015, the contents of which are incorporated into the present application in their entirety.

BACKGROUND

1. Field of the Invention

The present disclosure generally relates to medical devices. More particularly, the disclosure relates to a prosthesis comprising one or more sleeves useful during delivery of the prosthesis.

2. Description of the Related Art

Emergency or trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by emergency or trauma physicians to treat body vessel injuries include clamping the vessel with a hemostat, use of a balloon tamponade, ligation of the damaged vessel at or near the site of injury, or the insertion of one or more temporary shunts. However, conventional surgical repair is generally difficult with such actively bleeding, moribund patients. In many instances, there is simply not enough time to repair the body vessel adequately by re-approximating and suturing the body vessel. In many situations, the emergency physician will simply insert a temporary shunt (such as a Pruitt-Inahara Shunt) into the vessel. However, use of temporary shunts has been linked to the formation of clots. This may require returning the patient to the operating room for treatment and removal of the clots, often within about 36 to 48 hours of the original repair. Since shunts are generally placed as a temporary measure to restore blood flow and stop excessive blood loss, the shunt is typically removed when the patient has stabilized (generally a few days later) by a specialized vascular surgeon. After removal, the vascular surgeon will replace the shunt with a vascular graft, such as a fabric graft that is sewn into place. Ligation of the damaged blood vessel may result in muscle necrosis, loss of muscle function, or a potential limb loss or death.

Due to the nature of the body vessel injury that may be encountered, the use of shunts, repairing and/or ligating of a blood vessel often requires that such treatments be performed at great speed, and with a high degree of physician skill. Such treatments may occupy an undue amount of time and attention of the emergency physician at a time when other pressing issues regarding the patient's treatment require immediate attention. In addition, since the level of particularized skill required may exceed that possessed by the typical emergency physician, particularly traumatic episodes may require the skills of a physician specially trained to address the particular trauma, such as a vascular trauma, and to stabilize the patient in the best manner possible under the circumstances of the case.

U.S. Pat. No. 8,202,311, which is incorporated by reference into the present application in its entirety, discloses a device for repair of damaged portions of a body vessel. This device is suitable for placement within a blood vessel for repair of vascular trauma and restoration of blood flow through the vessel.

U.S. Pat. No. 8,721,710, which is incorporated by reference into the present application in its entirety, describes a docking head that is mounted on a graft having an outer diameter so as to couple the graft to a blood vessel without requiring the use of sutures. The docking head includes a hollow truncated cone having a passage that is adapted to correspond to the outer diameter of a graft and a plurality of outwardly pointing and inclined barbs. In operation, the conical structure followed by the graft is inserted into neck through its narrow end while inclined barbs smoothly pass through a portion of the neck. Upon pulling back the conical structure, inclined barbs are embedded within the neck, forming a firm and sealed connection between the vessel and the graft.

Trauma physicians generally find it difficult to manipulate a prosthesis for insertion into a body vessel that has been traumatically injured. For example, the injured vessel can be anywhere in the body, having different surrounding environments of bone structure, muscle tissue, blood vessels, and the like, which makes such obstructions difficult to predict in every situation and leaves the trauma physician working with an even further limited access opening. Another potential consideration is the amount of body vessel removed during a transection. The goal would be to remove a portion of the body vessel as small as possible.

Thus, what is needed is a delivery device for delivering a prosthesis for use in repair of an injured body vessel, such as an artery or a vein, during emergency open surgery. It would be desirable if such delivery device was easy for a trauma physician to use, and can rapidly introduce a prosthesis into a body vessel, thereby providing a conduit for blood or fluid within the injured body vessel.

BRIEF SUMMARY

The present disclosure relates to medical devices, methods of deployment of the same, and medical treatments using the medical devices.

In one aspect, a method of open surgical repair of a lacerated or transected body vessel to obtain fluid stability while maintaining fluid flow through the body vessel is disclosed. The method comprises the step of inserting a distal end of a prosthesis into a first vessel portion of the body vessel, wherein the prosthesis comprises a self-expanding stent and a graft body, the distal end of the prosthesis being retained in a radially compressed configuration with a distal end sleeve comprising a section having a thinner wall thickness and a section having a thicker wall thickness. The section having the thicker wall thickness is located proximally adjacent the section having the thinner wall thickness. The method also comprises the steps of applying an activating agent to the distal end sleeve and dissolving the distal end sleeve thereby allowing a distal end of the self-expanding stent to expand and engage the first vessel portion, the section having the thinner wall thickness dissolving before the section having the thicker wall thickness thereby allowing a distal-most end to expand and contact the vessel before the proximally adjacent portion. The method further comprises the steps of inserting a proximal end of the prosthesis into a second vessel portion of the body vessel, the proximal end of the prosthesis being retained in a radially compressed configuration with a proximal end sleeve comprising a section having a thinner wall thickness and a section having a thicker wall thickness, wherein the section having the thicker wall thickness is located distally adjacent the section having the thinner wall thickness, applying the activating agent to the proximal end sleeve, and dissolving the proximal end sleeve thereby allowing a proximal end of the self-expanding stent to expand and engage the second vessel portion, the section having the thinner wall thickness dissolving before the section having the thicker wall thickness thereby allowing a proximal-most end to expand and contact the vessel before the distally adjacent portion. The prosthesis comprising a longitudinal length sufficient to bridge and seal the laceration or bridge and interconnect the gap between the transection.

In another aspect, a method of open surgical repair of a lacerated or transected body vessel to obtain fluid stability while maintaining fluid flow through the body vessel is disclosed. The method comprises the step of inserting a distal end of a prosthesis into a first vessel portion of the body vessel, wherein the prosthesis comprises a self-expanding stent and a graft body, the distal end of the prosthesis being retained in a radially compressed configuration with a first sleeve and a second sleeve, wherein the first sleeve is located adjacent a distal-most end of the prosthesis and the second sleeve is located proximally adjacent the first sleeve, in series, at the distal end of the prosthesis. The first sleeve comprises a thinner wall thickness than the second sleeve. The method also comprises the steps of applying an activating agent to the first and second sleeves and dissolving the first and second sleeves thereby allowing a distal end of the self-expanding stent to expand and engage the first vessel portion, the first sleeve dissolving before the second sleeve thereby allowing the distal-most end to expand and contact the vessel before the proximally adjacent portion. The method also comprises the step of inserting a proximal end of the prosthesis into a second vessel portion of the body vessel, the proximal end of the prosthesis being retained in a radially compressed configuration with a third sleeve and a fourth sleeve, wherein the third sleeve is located adjacent a proximal-most end of the prosthesis and the fourth sleeve is located distally adjacent the third sleeve, in series, at the proximal end of the prosthesis. The third sleeve comprises a thinner wall thickness than the fourth sleeve. The method further comprises the steps of applying the activating agent to the third and fourth sleeves and dissolving the third and fourth sleeves thereby allowing a proximal end of the self-expanding stent to expand and engage the second vessel portion, the third sleeve dissolving before the fourth sleeve thereby allowing the proximal-most end to expand and contact the vessel before the distally adjacent portion. The prosthesis comprises a longitudinal length sufficient to bridge and seal the laceration or bridge and interconnect the gap between the transection.

In another embodiment, the present disclosure provides a prosthesis. The prosthesis comprises a self-expanding stent having a distal end, a middle portion, and a proximal end. The distal and proximal ends comprise one or more barbs. The prosthesis also comprises a graft body, wherein the distal end of the self-expanding stent comprises a radially compressed configuration and a distal end sleeve comprising a section having a thinner wall thickness and a section having a thicker wall thickness. The section having the thicker wall thickness is located proximally adjacent the section having the thinner wall thickness. The proximal end of the self-expanding stent comprises a radially compressed configuration and a proximal end sleeve comprising a section having a thinner wall thickness and a section having a thicker wall thickness. The section having the thinner wall thickness is located proximally adjacent the section having the thicker wall thickness and the distal end sleeve and the proximal end sleeve are dissolvable.

In some embodiments, a first sleeve comprises the section of the distal end sleeve having the thinner wall thickness and a second sleeve comprises the section of the distal end sleeve having the thicker wall thickness.

In some embodiments, the first and second sleeves are placed in series at the distal end of the prosthesis along the longitudinal axis.

In certain embodiments, a third sleeve comprises the section of the proximal end sleeve having the thinner wall thickness and a fourth sleeve comprises the section of the proximal end sleeve having the thicker wall thickness.

In some embodiments, the third and fourth sleeves are placed in series at the proximal end of the prosthesis along the longitudinal axis.

In some embodiments, the section of the distal end sleeve having the thicker wall thickness comprises two or more overlapping sleeves.

In certain embodiments, the section of the proximal end sleeve having the thicker wall thickness comprises two or more overlapping sleeves.

In some embodiments, the proximal end sleeve comprises a single sleeve and the distal end sleeve comprises a single sleeve.

The present disclosure also relates to a prosthesis comprising a self-expanding stent having a distal end, a middle portion, and a proximal end, the distal and proximal ends comprising one or more barbs. The prosthesis also comprises a a graft body wherein the distal end of the self-expanding stent comprises a radially compressed configuration and a distal end sleeve comprising a section having a thinner wall thickness and a section having a thicker wall thickness, wherein the section having the thicker wall thickness is located proximally adjacent the section having the thinner wall thickness. The prosthesis also comprises a first tube located distally adjacent the distal end sleeve and a first cap disposed around the first tube and the distal end sleeve. The proximal end of the self-expanding stent comprises a radially compressed configuration and a proximal end sleeve comprising a section having a thinner wall thickness and a section having a thicker wall thickness, wherein the section having the thinner wall thickness is located proximally adjacent the section having the thicker wall thickness. A second tube is located proximally adjacent the proximal end sleeve and a second cap is disposed around the second tube and the proximal end sleeve, wherein the distal end sleeve and the proximal end sleeve are dissolvable.

In some embodiments, the proximal end of the first tube extends into a lumen of the distal end sleeve.

In some embodiments, a distal end of the second tube extends into a lumen of the proximal end sleeve.

The present disclosure also relates to a method of open surgical repair of a lacerated or transected body vessel to obtain fluid stability while maintaining fluid flow through the body vessel. The method comprises providing a prosthesis comprising a proximal end and a distal end, the proximal end comprising a proximal end sleeve, a first tube located proximally adjacent the proximal end sleeve, and a first cap disposed around the first tube and the proximal end sleeve. The distal end of the prosthesis comprises a distal end sleeve, a second tube located distally adjacent the distal end sleeve, and a second cap disposed around the second tube and the distal end sleeve. The method also comprises the steps of removing the second cap and the second tube and inserting the distal end of the prosthesis into a first vessel portion of the body vessel, wherein the prosthesis comprises a self-expanding stent and a graft body. The distal end of the prosthesis is retained in a radially compressed configuration within the distal end sleeve, the distal end sleeve comprising a section having a thinner wall thickness and a section having a thicker wall thickness, wherein the section having the thicker wall thickness is located proximally adjacent the section having the thinner wall thickness. The method also comprises the steps of applying an activating agent to the distal end sleeve and dissolving the distal end sleeve thereby allowing a distal end of the self-expanding stent to expand and engage the first vessel portion, the section of the distal end sleeve having the thinner wall thickness dissolving before the section having the thicker wall thickness thereby allowing a distal-most end of the stent to expand and contact the vessel before a proximally adjacent portion.

Next, the method comprises removing the first cap and the first tube and inserting the proximal end of the prosthesis into a second vessel portion of the body vessel, the proximal end of the prosthesis being retained in a radially compressed configuration within the proximal end sleeve comprising a section having a thinner wall thickness and a section having a thicker wall thickness, wherein the section of the proximal end sleeve having the thicker wall thickness is located distally adjacent the section having the thinner wall thickness. The method further comprises the step of applying the activating agent to the proximal end sleeve and dissolving the proximal end sleeve thereby allowing a proximal end of the self-expanding stent to expand and engage the second vessel portion, the section of the proximal end sleeve having the thinner wall thickness dissolving before the section having the thicker wall thickness thereby allowing a proximal-most end of the stent to expand and contact the vessel before a distally adjacent portion. The prosthesis comprises a longitudinal length sufficient to bridge and seal the laceration or bridge and interconnect the gap between the transection.

In some embodiments, a first sleeve comprises the section of the distal end sleeve having the thinner wall thickness and a second sleeve comprises the section of the distal end sleeve having the thicker wall thickness.

In some embodiments, the first and second sleeves are placed in series at the distal end of the prosthesis along the longitudinal axis.

In some embodiments, a third sleeve comprises the section of the proximal end sleeve having the thinner wall thickness and a fourth sleeve comprises the section of the proximal end sleeve having the thicker wall thickness.

In some embodiments, the third and fourth sleeves are placed in series at the proximal end of the prosthesis along the longitudinal axis.

In some embodiments, the section of the distal end sleeve having the thicker wall thickness comprises two or more overlapping sleeves.

In some embodiments, the section of the proximal end sleeve having the thicker wall thickness comprises two or more overlapping sleeves.

In some embodiments, the proximal end sleeve comprises a single sleeve and the distal end sleeve comprises a single sleeve.

In some embodiments, the distal and proximal ends of the prosthesis each comprise one or more barbs to engage tissue of the body vessel to fix the distal and proximal ends to the first and second vessel portions.

In some embodiments, the proximal end sleeve and the distal end sleeve comprise hydroxypropyl methylcellulose.

In some embodiments, the body vessel is transected, the prosthesis being inserted into the first and second vessel portions through the gap between the transected vessel portions.

In some embodiments, the prosthesis is implanted permanently in the body vessel thereby obviating further surgical intervention or repair.

In some embodiments, the method further comprises clamping the first and second vessel portions to restrict fluid flow prior to inserting the distal and proximal ends of the prosthesis.

In some embodiments, a ratio of a wall thickness of the section of the distal end sleeve having the thicker wall thickness to the section of the distal end sleeve having the thinner wall thickness is from about 1.2:1 to about 4:1, and a ratio of a wall thickness of the section of the proximal end sleeve having the thicker wall thickness to the section of the proximal end sleeve having the thinner wall thickness is from about 1.2:1 to about 4:1.

In some embodiments, the distal end of the prosthesis comprises one or more barbs covered by the section of the distal end sleeve having the thinner wall thickness and the proximal end of the prosthesis comprises one or more barbs covered by the section of the proximal end sleeve having the thinner wall thickness.

In some embodiments, the activating agent is saline.

In some embodiments, the sections of the proximal end sleeve and the distal end sleeve having the thinner wall thicknesses dissolve in less than about 5 to about 10 seconds after the activating agent is applied and the sections of the proximal end sleeve and the distal end sleeve having the thicker wall thicknesses dissolve in about 8 to about 13 seconds after the activating agent is applied.

Additionally, the present disclosure relates to a method of forming a temporary seal between an outer surface of a self-expanding structure and a surrounding body. The method comprises disposing a dissolvable sleeve comprising hydroxypropyl methylcellulose around a radially compressed annular space of the self-expanding structure, placing at least a portion of the dissolvable sleeve within a lumen of the surrounding body, and exposing the dissolvable sleeve to an activating agent, whereby the activating agent causes a portion of the dissolvable sleeve to dissolve to a degree where the radially compressed annular space expands and engages an inner wall of the surrounding body, wherein an undissolved but hydrated gel portion of the sleeve forms a temporary seal between the outer surface of the self-expanding structure and the inner wall of the surrounding body.

In some embodiments, the temporary seal remains in place for about 3 seconds to about 1 week.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which:

FIG. 2A is a plan view of the body of a vascular conduit according to a disclosed embodiment, in an unrolled configuration.

FIG. 2B is an enlarged plan view of a portion of the vascular conduit in FIG. 2A.

FIG. 4A is an enlarged elevation view of a barb of a vascular conduit, in a deployed configuration.

FIG. 4B is an enlarged elevation view of a barb of a vascular conduit, in a delivery configuration.

DETAILED DESCRIPTION

Figure 1:
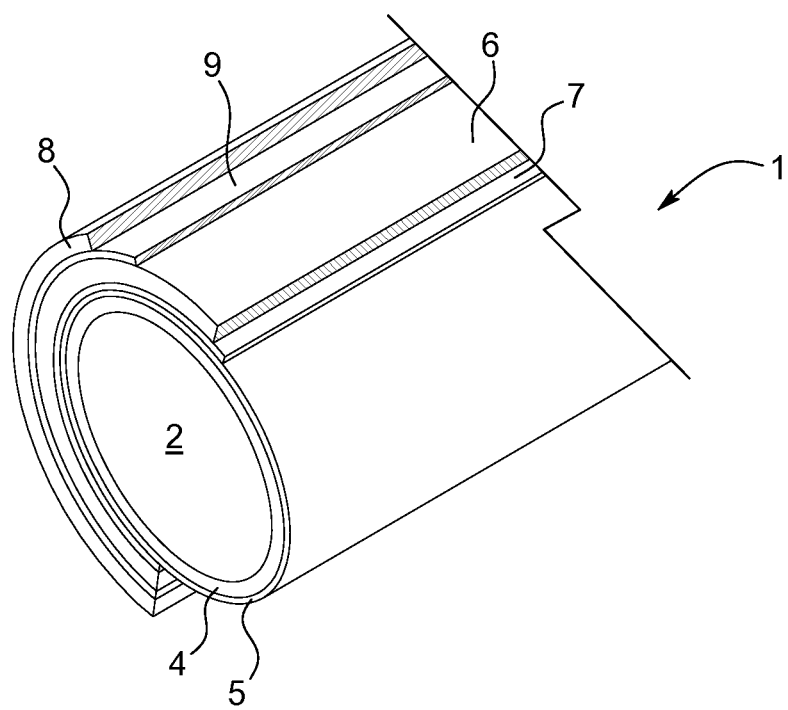
FIG. 1 is a sectional view of a blood vessel that schematically illustrates the orientation of the layers of the blood vessel.

Various embodiments are described below with reference to the drawings. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as conventional fabrication and assembly.

The device disclosed herein may be useful for repair of a body vessel, such as a blood vessel, during an emergency open surgical procedure. This device can be particularly useful for repair of a lacerated or transected artery or vein during emergency surgery, and particularly, to obtain hemostasis while maintaining blood perfusion. While some devices are only implanted temporarily for treatment, the presently disclosed device may be implanted permanently thereby obviating the need for further surgical intervention and repair. Further, the presently disclosed device may be used in accordance with an open surgical procedure, which is distinguished from an intraluminal procedure.

In an open surgical procedure, the physician accesses the target site within the body from an opening in the skin of the patient's body, usually directly over the target site. In an intraluminal procedure, which may be considered "minimally-invasive" as compared to an open surgical procedure, the physician makes one or more incisions to insert a tube having an open end outside of the patient's body and another open end at the target site within the patient's body. The tube allows the physician to deploy various surgical instruments to the target site to perform a surgical procedure.

In order to understand the structure and operation of the inventive device, a brief description of the structure of a blood vessel in the body will be helpful. Blood vessels are of two types, namely arteries and veins. Generally speaking, arteries are elastic vessels that carry oxygenated blood away from the heart, and veins are elastic vessels that transport blood to the heart that then transport blood to the lungs for oxygenation. The walls of both arteries and veins generally consist of three layers or tunics. The inner layer is referred to as the tunica intima, which is composed of endothelium and delicate collagenous tissue. The middle layer is referred to as the tunica media, which is composed of typically a muscular layer, and consists of smooth muscle and elastic fibers. The outer layer is referred to as the tunica adventitia, which is the outer covering of the vessel, and is composed of connective tissue, collagen, and elastic fibers. The tunic adventitia includes small vessels, referred to as vasa vasorum, which supply nutrients to the tissue.

FIG. 1 is a sectional view of a blood vessel (1) that schematically illustrates the orientation of these layers. Vessel (1) includes a lumen (2) extending therethrough for transport of blood. The respective tunica intima (4), tunica media (6), and tunica adventitia (8) extend radially outwardly from the lumen (2). The tunica intima (4) includes a thin layer of connective tissue (5) (often referred to as the basement membrane) in the region where it joins the tunica media (6). A thin layer of internal elastic lamina (7) may also be found between the tunica intima (4) and the tunica media (6). Another thin layer of external elastic lamina (9) may also be found between the tunica media (6) and the tunic adventitia (8). The illustration and accompanying explanation provided hereinabove is only intended to be a very brief explanation of the structure of a blood vessel. Those skilled in the art will appreciate that the relative thickness of a particular layer will vary from that shown schematically in FIG. 1, and that the thickness of various layers will also vary depending upon whether the vessel is an artery or a vein. In each instance, however, the vessel should include the three layers illustrated in FIG. 1. It is believed that those skilled in the art will have sufficient appreciation for the basic vessel structure that further explanation is unnecessary to achieve an understanding of the present invention.

In some embodiments, a vessel may have an inner diameter (or outer lumen diameter) from about 3 mm to about 11 mm, such as from about 5 mm to about 9 mm.

In some embodiments, the device disclosed herein comprises a barbed, self-expanding vascular repair graft. This device may also be referred to herein as a "vascular conduit" or "prosthesis". The device comprises a conduit to allow blood flow therethrough. The device may include a generally tubular conduit body, a plurality of barbs along a portion of the conduit body, one or more sleeves, and a graft covering. The conduit body may be expandable between a radially compressed, delivery configuration and a radially expanded, deployed configuration. The graft covering may extend along a luminal wall of the conduit body and along a portion of an exterior surface of the conduit body. The prosthesis has a size and a shape suitable for placement within a body vessel, such as an artery or vein, and particularly, for placement at the site of a vascular trauma.

The conduit body defines a lumen about a longitudinal axis, between a distal end and a proximal end of the conduit body. The conduit body may have a substantially circular cross-section having any outer diameter in the expanded configuration suitable for body vessels, such as about 5 mm, to engage the luminal surface of the body vessel wall. Although a substantially circular cross-section is generally preferred, the cross-section of the body may be elliptical or other shapes known by one skilled in the art to be used in a body vessel.

In some embodiments, the outer diameter of the uncompressed, expanded prosthesis may be from about 4 mm to about 12 mm, such as from about 6 mm to about 10 mm. The outer diameter should be selected such that it will fit within an overlapping vessel lumen. In its radially compressed configuration, the prosthesis may have an outer diameter from about 2 mm to about 4 mm, such as from about 2.7 mm to about 3.3 mm.

The length of the prosthesis can be selected by one of ordinary skill in the art depending upon the length necessary to repair the defect in the vessel and achieve hemostasis. In some embodiments, the length may be from about 5 cm to about 20 cm, such as from about 10 cm to about 15 cm.

The general length of the prosthesis/conduit body may depend upon the size of the laceration or puncture wound opening in the vessel. The length of the conduit body is at least as long as the laceration in the vessel, if not longer, in order for barbs to penetrate and engage securably to an uncompromised portion of the vessel. If the vessel is transected, the length of the conduit body is at least long enough so that each end of the transected vessel may be joined to a respective end of the conduit body.

The conduit body can be any pattern of stent structures known in the art. For example, the conduit body may comprise the pattern shown in FIGS. 2A and 2B. The conduit body may be composed of a proximal portion, a distal portion, and an intermediate portion connected to the proximal and distal portions by a plurality of axial struts. The intermediate portion may be positioned along a laceration or the intermediate portion may be positioned between each end of a transected vessel.

In some embodiments, the proximal portion may be axially spaced from the intermediate portion by a first gap, while the distal portion may be axially spaced from the intermediate portion by a second gap. The gaps may be annular gaps with one or more longitudinal struts spanning the gap in order to connect the distal and proximal portions to the intermediate portion. The longitudinal length of the proximal and distal portions may be same length, or may be different lengths, as will be appreciated by those skilled in the art.

The conduit body can be formed of a biocompatible metal, such as stainless steel (e.g., 316L SS), titanium, tantalum, nitinol or other shape memory materials, or a high-strength polymer. To form alternating longitudinal segments from a metal cannula or sheet, material must be removed in some manner, such as by commercially available computer-controlled laser, leaving a framework of integrated support members that has a small surface area relative to the initial surface area of the cannula or sheet. Other methods of manufacture include chemical etching, machining, electrode discharge machining or cutting with a water jet. Finishing techniques can also be used to remove some material, e.g., electropolishing or grinding.

With respect to FIGS. 2A and 2B, an embodiment of the conduit body (140) is shown having alternating hoop cells (82) and flex cells (124) throughout the majority of the intermediate portion (24). The hoop cells (82) may have a series of hoop struts (86) connected to each other through a series of hoop bends (92). The hoop cells (82) may also have longitudinal struts (90) that extend substantially through the entire length of the hoop cells (82). The longitudinal struts (90) connect the hoop cells (82) and flex cells (124) together so that about half of the longitudinal struts (90) connect to the proximally adjacent flex cell (124) and the other half of the longitudinal struts (90) connect to the distally adjacent flex cell (124). Thus, each longitudinal strut (90) may be connected at one end to the outside of an adjacent flex cell bend (94), which connects two flex struts (122) together, and is connected at the other end to the inside of a hoop cell bend (92), which connects two hoop struts (86) together.

The flex cells (124) have a series of flex struts (122) connected to each other through a series of bends (94). Because the longitudinal struts (90) do not extend substantially through the length of the flex cells (124), the flex cells (124) only have flex struts (122) within each flex cell (124).

In some embodiments, the overall length of the flex cells (124) is substantially the same as the overall length of the hoop cells (82). For example, overall length of the flex cells (124) and the hoop cells (82) is measured from the outside of opposite bends (92,94) and may be about 2.2 mm to about 2.5 mm. However, it is possible that the overall length of the flex cells (124) may be slightly longer than the overall length of the hoop cells (82), since the extra width of the flex struts (122) may also be applied to the flex cell bends (94).

The proximal and distal ends of the conduit body (140) may comprise end cells (96). The end cells (96) may have longitudinal struts (90) that extend through the end cells (96) to connect each end cell (96) to an interior barbed cell (142). A series of longitudinal struts (112) extends across the gaps (30,32) to connect the barbed cells (142) to the first intermediate cells (144).

As can be seen in FIGS. 2A and 2B, the barbed cells (142) may be the second end cells located adjacent the first end cells (96). Structurally, the barbed cells (142) may have barbs (14) deflected outward like FIGS. 3A and 3B. In some embodiments, the width of the struts (126,146) in the barbed cells (142) is wider than the width of the struts in the first end cell (96) and the struts (86,122) in the hoop and flex cells (82,124). However, the width of the struts (126,146) may be substantially equal to the width of the struts in the first intermediate cell (144).

The barbed cells (142) are each connected to a first intermediate cell (144) in the intermediate portion (24) with longitudinal struts (112). The longitudinal struts (112) may be connected to non-barbed struts (146) in the barbed cells (142) at the same end that the struts (126) are connected to the barbs (14).

In a conduit body (140) designed to expand from about 5 mm to about 7 mm, or nominally about 6 mm, the length (148) of the first end cells (96), first intermediate cells (144), hoop cells (82) and flex cells (124) may be from about 1.9 mm to about 2.5 mm. In one particular embodiment, the length is about 2.2 mm.

In a conduit body (140) designed to expand from about 7 mm to about 9 mm, or nominally about 8 mm, the length (148) of the first end cells (96), first intermediate cells (144), hoop cells (82) and flex cells (124) may be from about 2.0 mm to about 2.6 mm. In one particular embodiment, the length is about 2.3 mm.

In a conduit body (140) designed to expand from about 9 mm to about 11 mm, or nominally about 10 mm, the length (148) of the first end cells (96), first intermediate cells (144), hoop cells (82) and flex cells (124) may be from about 2.5 mm to about 3.1 mm. In one particular embodiment, the length is about 2.8 mm.

The length of the cells is preferably measured from the outer surface of opposing bends as shown in FIG. 2B. The length (150) of the barbed cells (142) is preferably longer than the length (148) of the first end cells (96), first intermediate cells (144), hoop cells (82) and flex cells (124) as measured from the outer surface of the bend (132) adjacent the first end cell (96) and a corresponding opposing imaginary bend (152) defined at the connection of the longitudinal struts (112) or the barbs (14).

For example, for a conduit body (140) designed to have an expanded diameter from about 5 mm to about 9 mm, or nominally about 6 mm or about 8 mm, the length (150) of the barbed cells (142) may be about 2.2 mm to about 2.8 mm. In one particular embodiment, the length is about 2.5 mm.

In a conduit body (140) designed to have an expanded diameter from about 9 mm to about 11 mm, or nominally about 10 mm, the length (150) of the barbed cells (142) may be about 2.8 mm to about 3.4 mm, or about 3.1 mm. In some embodiments, the length (150) of the barbed cells (142) is about 5% to about 15% longer than lengths (148) of the first end cells (96), first intermediate cells (144), hoop cells (82) and flex cells (124).

An advantage of the conduit body (140) of FIGS. 2A-2B is that the barbed cells (142) are located closer to the ends of the conduit body (140). This is helpful because the conduit body may be used in emergency settings to reconnect fully transected vessels. In this procedure, the ends of the conduit body may be inserted into opposing transected ends of a vessel to stop hemorrhaging and regain blood flow through the vessel. This type of procedure will typically be an open surgical procedure, where the conduit body is placed directly into the wound site and the ends of the conduit body are inserted directly into the separated ends of the transected vessel. In this type of procedure, it is desirable to minimize the portion of the conduit body that must be inserted into the transected vessel ends. Thus, it would be preferred to locate the barbs (14) close to the ends of the conduit body, since the barbs are intended to engage the inner wall of the transected vessel to secure the conduit body to the vessel.

Although it is desirable to have the barbed cells (142) as close as possible to the ends of the conduit body, it is preferred to have a first end cell (96) at the very ends of the conduit body before the barbed cells, since the first end cells expand the vessel lumen of each transected end and provide the barbed cells with smoothly expanded vessel sections to secure the barbs against.

The conduit body (140) of FIGS. 2A-2B is also advantageous because the barbs (14) are located within the gaps (30,32) created by the longitudinal struts (112) connecting the barbed cells (142) and the first intermediate cells (144).

As described above, the longitudinal struts connecting the barbed cells and the first intermediate cells create a gap between the barbed cells and the intermediate cells, since the longitudinal struts do not extend through the barbed cells or the first intermediate cells like the longitudinal struts (90) of the hoop cells (82). The gaps between the barbed cells and the first intermediate cell may be larger than all other gaps in the conduit body between adjacent cells. However, because the barb tips (43) are located within this larger gap (30,32), the extra space is efficiently used and a compact barb arrangement is provided.

The presence of barbs (14) permits the prosthesis to be secured to the tissue of the vessel during a medical procedure. In particular, barbs (14) provide vessel fixation while avoiding adverse conditions associated with disturbing the vasa vasorum and/or pressure induced necrosis of the medium muscular arteries of the type that may result from tying ligatures circumferentially around a connector or a prosthesis. Barbs (14) can further include various shaped member structures, including fibers, bristles, or outer protruding and penetrable media. It is noted that the barbs in the Figures are enlarged in order to illustrate the general shape of the barbs and may not accurately reflect the true size of the barbs in relation to the prosthesis or connector.

Barbs (14) can be sized and shaped in any manner to enable a secure connection with the vessel that is sufficient to inhibit migration of a prosthesis within the vessel. It is desirable, however, that barbs (14) are sized and shaped such that they may penetrate the tunica intima (4), the basement membrane (5), and partially enter the tunica media (6) (see FIG. 1). It is preferable that any portion of barbs (14) do not enter the tunica adventitia, and more importantly, do not disturb or otherwise adversely affect the vasa vasorum. A fibrotic response can be created within the penetrated portions of the blood vessel, which further anchors the prosthesis in the vessel over time. Alternatively, the barbs (14) may only partially penetrate the vessel layers and/or may only apply outward pressure against some or all of the layers.

A wide variety of configurations for barbs (14) are provided in order to better secure the prosthesis with the tissue. Barbs (14) can be constructed to have varying dimensions, such as length, base width, thickness, barb angle, orientation, distribution, sharpness, and point (tip) configuration. These dimensional configurations can aid in selecting the degree of penetration into the vessel wall, and preferably, to restrict penetration through only the tunica intima and partially into the tunica media layers as described. For example, barbs (14) may be configured to penetrate the wall of the body vessel without cutting through the body vessel. In other examples, barbs (14) can be also configured to seat within the body vessel wall securely as to not further propagate or cut radially once engaged.

Figure 3B:
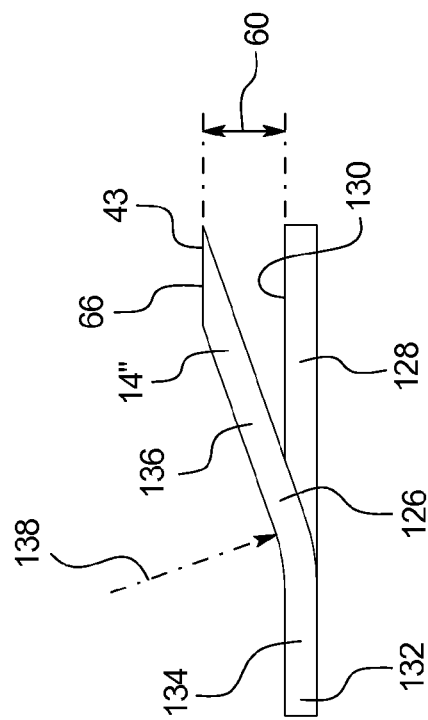
FIG. 3B is an enlarged elevation view of another barb of the vascular conduits.
Figure 3A:
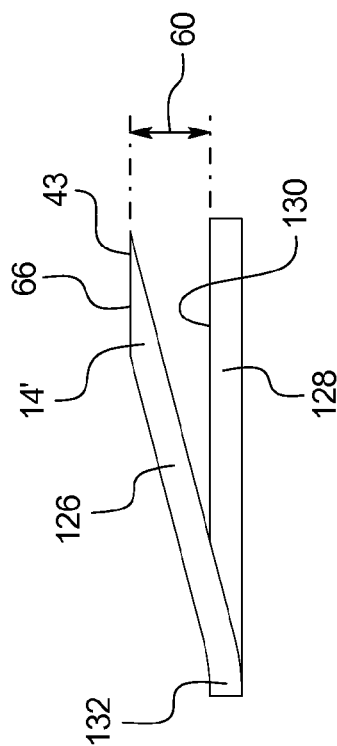
FIG. 3A is an enlarged elevation view of a barb of the vascular conduits.

FIG. 3A illustrates one embodiment of the barbs (14'). The barbs (14') may be formed by deflecting the struts (126) in the barbed cells (142) that are attached to the barbs (14') radially outward from the outer circumference (130) of the stent structure. Since the struts (128) in the barbed cells (142) that are connected to the hoop cells (82) with longitudinal struts (90) do not have barbs (14'), these struts (128) are not deflected outward and remain within the outer circumference (130) defined by the stent structure.

As shown in FIG. 3A, the barbs (14') and struts (126) attached thereto are deflected outward along substantially the entire length of the struts (126). That is, the struts (126) are deflected outward from the bends (132) opposite of the barbs (14') to the barb tips (43). As described above, the barbs (14') may also include flattened surfaces (66) that are generally parallel to the axis of the stent structure and/or the outer circumference (130) of the stent, when the barbs (14') are in their outward deflected configuration. The barbs (14') may extend outward from the outer circumference (130) of the stent so that the penetration depth (60) is about 0.25 mm to about 0.75 mm, or about 0.5 mm. For example, this may be measured from the outer surface of the adjacent struts (128) connected to the hoop cells (82) and the outer flattened surfaces (66) of the barbs (14').

Preferably, the barbs (14') are formed by outwardly deflecting the struts (126) connected to the barbs (14'), and then heat setting the struts (126) in the deflected state. For example, where the stent structure is made from nitinol, the stent structure may be expanded with a mandrel to its expanded configuration and the struts (126) attached to the barbs (14') may be deflected outward from the mandrel. The stent structure may then be heated so that the stent structure retains this expanded and deflected configuration as the unstressed state of the stent.

If desired, the barbs (14') may be ground after deflecting and heat setting the barbs (14') and struts (126) to form the flattened outer surfaces (66). The stent structure may then be elastically compressed to a smaller diameter to achieve a lower profile for delivery through a body vessel (1,100). It may also be preferable for delivery to elastically compress the barbs (14') and struts (126) connected thereto inwardly so that the barbs (14') and struts (126) are aligned within the smaller diameter of the stent and not extending outwardly therefrom. Accordingly, when the stent is released at a treatment site, the stent structure will self-expand to the unstressed expanded configuration and the barbs (14') and struts (126) will expand to the outwardly deflected configuration.

FIG. 3B illustrates another embodiment of the barbs (14"). In contrast to the barb (14') shown in FIG. 3A, the barb (14") shown in FIG. 3B is not deflected outward along the entire length of the struts (128). Instead, a non-deflected portion (134) of each strut (128) in the barbed cells (142) remains within the outer circumference (130) of the stent structure. Thus, the barbs (14") are formed by the flexing only a portion (136) of the struts (128) in the barbed cells (142) radially outward. Preferably, the initiation of the deflected portion (136) may start at about 25% to about 50% of the length of the struts (128) from the bends (132) opposite of the barbs (14"). In addition, it is preferable for the barbs (14") to be deflected along a radius (138) of about 0.5 mm to about 1.5 mm. Like the barbs (14') of FIG. 3A, it is preferable for the penetration depth (60) to be about 0.25 mm to about 0.75 mm, or about 0.5 mm.

In FIG. 3B, the non-deflected portion (134) of the struts (126) for a conduit body (140) designed to expand to about 5 mm up to about 9 mm, or nominally to about 6 mm or about 8 mm, is, in some embodiments, about 0.5 mm to about 1.1 mm. In one embodiment, it is about 0.8 mm. The non-deflected portion (134) of the struts (126) for a conduit body (140) designed to expand to about 9 mm up to about 11 mm, or nominally to about 10 mm, is, in some embodiments, about 1 mm to about 1.8 mm. In one embodiment, it is about 1.4 mm. In some embodiments, the non-deflected portion (134) extends about 15% to about 50% along the entire length of the struts (126) as measured from the bends (132) to the barb tips (43). The length (154) of the barbs from the imaginary bends (152) is, in some embodiments, about 0.3 mm to about 0.8 mm. In one embodiment, it is about 0.55 mm. The length (156) of the longitudinal struts (112) connecting the barbed cells (142) and the first intermediate cells (144) measured from imaginary bend (152) to imaginary bend (152) is, in some embodiments, about 0.55 to about 1.05 mm. In one embodiment, the length is about 0.8 mm. The length (158) of the space between the barb tips (43) and the adjacent bends in the first intermediate cells (144) is, in some embodiments, about 0.1 mm to about 0.6 mm. In one embodiment, the length is about 0.3 mm.

Figure 4C:
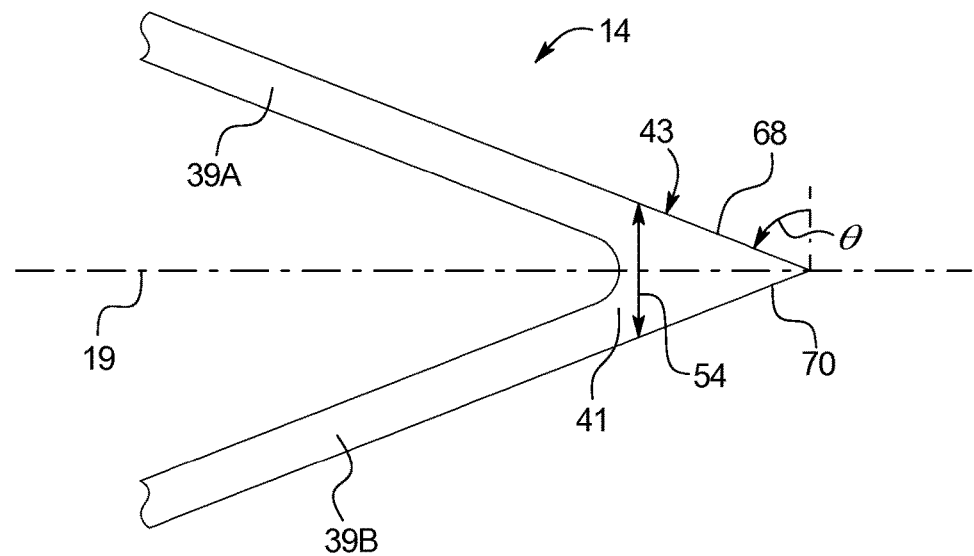
FIG. 4C is an enlarged plan view of a barb of a vascular conduit, in a deployed configuration.

Referring to FIGS. 4A-4C, the general length (52), angle α, base width (54) and thickness (56) of barb (14) can vary depending on the vessel type and characteristics. For example, for a prosthesis having an outer diameter of 6 mm, barbs (14) can have a length (52) in the range between about 0.1 mm to 1 mm, such as about 1 mm, where the length is measured from intersection of the base of the barb (14) with the bend (41) to the barb tip (43). Base width (54) typically depends on the size of the bends and strut thickness. The number of barbs (14) can have a range from about 2 to about 20, although any number suitable for implantation of the prosthesis is within the scope. As a result, base width (54) can be in the range between about 0.2 mm or less to about 0.4 mm or more, such as about 0.8 mm.

Referring to FIG. 4A, the angle α of barb (14) in the deployed configuration is preferably selected to orient barb (14) radially outward away from longitudinal axis (19) in a manner to prevent penetration into the tunica adventitia. Optionally, barb (14) may be configured to penetrate at a certain depth (60) into the vessel wall as to avoid the tunic adventitia. Although it is preferable that all of barbs (14) have a substantially similar angle α, or similar depth (60) penetration, it can be appreciated by one skilled in the art that barbs (14) having varying angles, or depth penetrations (60), may be advantageous. Angle α of about 5 degrees to about 30 degrees is preferred, although an angle of up to about 45 degrees to 60 degrees may also be used in some applications depending on the length (52) of the barb and the preferred depth (60) penetration. For example, angle α of barb (14) may be oriented at about 20 degrees to about 30 degrees, such as about 25 degrees. The suitable barb length, angle, and/or depth penetration can be determined by the vessel type and other considerations taken into account by one of ordinary skill in the art.

Barbs (14) can move between a delivery configuration and a deployed configuration. For instance, when the conduit body is in the radially compressed configuration, as shown in FIG. 4B, barbs (14) are surprisingly in substantial alignment with the longitudinal axis (19). Otherwise, the barbs would still be extending radially outward when the conduit body is in the radially compressed configuration, resulting in an increased risk that the barbs may be compromised or damaged during delivery or extend through a delivery sleeve. This arrangement can facilitate delivery of the prosthesis as the barbs are in a location to not interfere with an outer catheter wall during its relative movement for delivery. During radial expansion of the conduit body to the radially expanded configuration, barbs (14) can pivot radially outward to the deployed configuration, which is shown in FIG. 4A.

In some embodiments, only barbs (14) and the region generally around it extend radially outward instead of the barbs and first and second struts (39A,39B). To this end, the prosthesis is generally cylindrical with the barbs engaging into the body vessel. When struts (39A,39B) also extend outward, there is an increased risk of irritation to the body vessel, as well as pockets formed from the separation of the body vessel from the prosthesis body.

Tip (43) of barbs (14) may be formed by one or more angled cuts to create a bi-angled tip, as shown in FIG. 4C.

The cuts forming tip (43) can have edges (68,70) that may be cut at different or the same angle Θ. Angle Θ may range from about 15 degrees to about 60 degrees relative to longitudinal axis (19), although the angle Θ for one edge of edges (68,70) can be substantially parallel to longitudinal axis (19). Edges (68,70) can be rounded, or otherwise made dull, to decrease the risk of the edges from cutting radially within the body vessel tissue once engaged. Techniques for making edges rounded and dull can be by abrasive treatment, chemical treatment, abrasive blasting, and/or electropolishing. It is preferred to have tip (43) with a complex-angle, where, when barb (14) is angled at a predetermined angle α, tip (43) has a surface (66) generally parallel to the longitudinal axis (19), as shown in FIG. 4A.

Surface (66) can be formed by removing a portion (64), represented by the dashed lines, from the tip. Although removed portion (64) is shown to be at the outward surface of tip (43), the inner surface of tip (43) can instead be ground to create a surface generally parallel. Alternatively, surface (66) may be arcuate after being ground to be concave outwardly or inwardly depending on which side of the tip is ground. This can allow barb tip (43) to be sharpened without sharpening edges (68,70) along the length of barbs (14). Optionally, instead of removing portion (64), a distal portion may be formed by forming barb (14) with a bent portion at tip (43), or by bending barb (14) at tip (43), to create a surface or portion that is substantially parallel to the longitudinal axis (19). Surface (66) or bent portion can allow for easier penetration into the wall of the vessel to a limited depth (60) or distance into the innermost layer(s) of the body vessel wall, without passing through the body vessel.

Barbs (14) may have a region, preferably along its tip (43), with a controlled porosity to allow for tissue in-growth as well as delivery of drugs or growth factors and other tissue modulators. For example, collagen-based formulations can be used to provide a growth and attachment matrix. There can also be features (e.g., bioremodelable materials, such as SIS) placed strategically around the cylindrical conduit body and/or barbs (14) of the prosthesis to promote tissue attachment.

Barbs (14) can be distributed along all or part of the circumference of conduit body in an orderly, or a random, fashion. Some configurations of barbs can be measured in terms of maximum load and maximum extension at maximum load with an axial tensile test. One such test includes affixing one end of a flexible prosthesis having a 6 mm (0.24 inch) outer diameter for anchoring into the vessel. A general tensile rate of 12.7 cm/minute (5 inches/minute) is applied to one of the ends while measuring the tensile load and extension from the position from start of test to position at maximum load. The maximum tensile load measured in the range of about 1.1 to about 5.1 N (2.4±1.6 N) and the extension at maximum tensile load measured in the range of 13.8 mm to about 42.7 mm (27.2±12.7 mm).

Those skilled in the art are well aware of suitable means for fabricating structures, such as barbs, having a desired size and shape from substrate structures, such as a cylindrical body or ring of biocompatible material, or alternatively, for incorporating barbs into a cylindrical body. Preferably, the barbs are made of a rigid material. One particularly favored method of fabrication is laser cutting. Other methods such as chemical etching or micro-machining may also be used. Nano-fabrication may also be an acceptable way of forming small barbs. Other barbs have been fabricated by building out layers of silicon to form barbs in the range of 100 microns high by 80 microns wide, which structures resemble slanted pyramids.

Barbs can be made of the same material as conduit body, or be a different material. As discussed previously, the material can be stainless steel or nitinol, among others. When incorporating barbs to conduit body, it may be desirable that the material of the barbs be the same as the material of the conduit body. The barb tips can be cut, and then attached to the conduit body through known means of welding, soldering, or the like.

As described above, a graft (graft covering) may be applied to the conduit body to prevent blood flowing through the lumen of the conduit body from passing through the wall of the conduit body. The graft may be in intimate contact with the conduit body and in some embodiments, it may cover the conduit body. The graft covering can have a delivery configuration when the body is in the radially compressed configuration, and a deployed configuration when the body is in the radially expanded configuration. In some embodiments, in the delivery configuration, the graft may be in the radially expanded configuration or a middle portion of the graft may be in the radially expanded configuration. The graft can be a liner that extends entirely along the luminal wall of the conduit body. The graft covering can be made of material to inhibit fluid or blood located within the prosthesis lumen from passing through the graft covering. In other words, fluid flow is urged by the graft covering to enter into one end and exit out of the end of the prosthesis. To better seal the ends of conduit body, a portion of graft covering can be applied at the end. In one example, at least one of a proximal end and a distal end of the graft covering can extend from a luminal wall and radially outward around the ends of the conduit body, such that the graft covering has a portion folded around at least one of the ends of the body. Each of the ends may then extend longitudinally along the exterior surface of the conduit body.

In some embodiments, the ends extend to the respective gaps (30,32) where it then can be attached to itself. As a result, the longitudinal distance of each of the first and second gaps (30,32) should be long enough to allow plenty of the graft covering to attach to itself for a secure attachment. In this aspect, the exterior surface of intermediate portion (24) is left with bare material (i.e., without graft covering along the exterior surface) facing the vessel wall. This arrangement is found to stimulate neointimal or endothelial cell growth along this portion which can be beneficial for healing the vascular defect.

Further, the graft covering along the interior surface along the intermediate portion can inhibit the degree of cell growth into the lumen of the prosthesis for inhibiting thrombosis of the prosthesis. The graft covering, as well as the conduit body, along the intermediate portion can also include a therapeutic agent described below to inhibit thrombosis and to accelerate cell growth and healing. The graft covering can attach to itself with a sufficient amount of the combination of pressure and heat for such purpose. Optionally, the graft covering can also be sutured to one another or may even be sutured to the conduit body. In another example, the graft covering can be applied to the tubular body with electro-spinning.

A graft may be attached to the conduit body in any manner desired, depending upon the particular application. In some embodiments, the prosthesis may have an outer graft layer that only partially covers the conduit body and is adhered to the inner layer. Although the inner graft layer may be made of various materials and may be applied by various methods, the inner layer, in some embodiments, is made of an inner porous layer and an outer non-porous layer.

For example, the inner porous layer, which forms the luminal surface of the prosthesis, may be applied to a mandrel by dip coating the mandrel in a mixture of polyurethane or Thoralon®, a solvent, and a salt. A solvent is preferably used with the polyurethane or Thoralon® in applying each of the layers to maintain the desired viscosity and to cause mixing between each of the layers to bond the layers together. The porous layer is preferably formed by removing the salt from the first inner layer by dissolving the salt in a bath. However, this process is preferably done after all of the graft layers are formed and cured so that the solvents used in forming and bonding the layers do not cause the pores to close. After the inner porous layer has cured, the mandrel may be dip coated a second time in a mixture of polyurethane or Thoralon® and a solvent to apply a non-porous layer around the outside of the porous layer. As noted, a solvent in the non-porous layer causes the polyurethane or Thoralon® of the two layers to mix together so that the two layers bond together after the non-porous layer has cured.

After the non-porous layer has cured, the conduit body (which may be primed with parylene) is mounted onto the mandrel in an expanded state. An outer layer may then be applied onto the outer surface of the conduit body. The outer layer may be made of a material that bonds to the inner layer through the open spaces in the wall of the conduit body. For example, a mixture that is substantially the same as the inner non-porous layer of polyurethane or Thoralon® and a solvent may be used for the outer layer, or other suitable polymers and compatible solvents may be used. As a result, the solvent causes the inner non-porous layer and the outer layer to mix together through the openings in the conduit wall. Thus, after curing, the two layers will be bonded together. Instead of dip coating as may be done for the inner layer, the outer layer may be applied through a nozzle that directs a narrow stream of polyurethane or Thoralon® and a solvent mixture onto the outer surface of the conduit body and the inner layer. The nozzle may then be translated as the mandrel and conduit body are rotated to apply a helical thread of graft material onto the conduit body. This prevents graft material from accumulating in the space underneath the deflected barbs.

The mixture may be supplied to the nozzle by an air pressure needle pump or a syringe pump. Preferably, the nozzle opening is between about 33 gauge to about 18 gauge. The overall thickness of the graft layers including the porous first inner layer, the non-porous second inner layer, and the outer layer is, in some embodiments, about 0.15 mm to about 0.8 mm. In one embodiment, it is about 0.39 mm.

The porous first inner layer may be thicker than the non-porous second layer and thicker than the outer layer. For example, the porous first inner layer may be about 0.10 mm to about 0.7 mm thick, and the non-porous second inner layer and outer layer may each be about 0.07 mm to about 0.2 mm thick.

In some embodiments, polyethylene terephthalate (PET) or Dacron® fabric may be used for the inner layer and a polyurethane or Thoralon® and a solvent mixture may be applied as the outer layer. Thus, in this case, the polyurethane and polyethylene terephthalate bond to each other because they are compatible with each other even though the inner and outer layers are not the same material.

In some embodiments, one or more of the end cells may be completely coated by the outer layer. This may be done by translating the nozzle along a short pitch so that adjacent windings of the outer layer flow together to form a contiguous outer layer. It may be desirable to apply the graft layers to a conduit body (140) as in FIG. 2A. When applied to the conduit body of FIG. 2A, the contiguous outer layer at the ends would preferably be shorter and only cover the first end cell (96) and part of the barbed cell (142). In some embodiments, the middle portion is only partially coated by the outer layer, which leaves the conduit body less constrained to permit improved flexibility along the middle portion.

In other embodiments, the outer layer may be applied as a helical thread along the middle portion with a pitch large enough so that adjacent windings do not contact each other. Thus, the space between the windings is uncovered by the outer layer, and the inner layer is only bonded to the outer layer along the path of the helical thread. One advantage of this embodiment is that the outer layer may be applied as a continuous process from the proximal end to the distal end.

The graft covering can be formed from conventional materials well known in the medical arts. It is preferred that the graft covering have a porosity for sufficient capillarization and be relatively thin as possible (e.g., about 0.0005 inches to about 0.010 inches, and preferably about 0.001 to about 0.0035 inches). Examples of pore density and pore size for the graft covering, as well as other types of materials for a graft covering can be found in U.S. Pat. No. 7,244,444, which is incorporated herein by reference in its entirety.

A specific example of a material is used to form the graft covering is expanded polytetrafluoroethylene (ePTFE). Other materials that may be suitable include, for example, polytetrafluoroethylene, electrospun PTFE, silicone, polyurethane, polyamide (nylon), as well as other flexible biocompatible materials. As noted above, the graft covering can also be formed from known fabric graft materials such as woven polyester (e.g. DACRON®), or from a bioremodelable material. One exemplary graft material is THORALON® from Thoratec Corporation, Pleasanton, Calif., that can prevent leakage of fluid through the pores of the graft. THORALON® is a polyetherurethane urea blended with a siloxane containing surface modifying additive, and has been demonstrated to provide effective sealing of textile grafts. Another example is polyethylene, and in particular, an ultra-high molecular weight polyethylene (UHMwPE), commercially available as DYNEEMA®.

The graft covering may also include a bioremodelable material that can provide an extracellular matrix that permits, and may even promote, cellular invasion and ingrowth into the material upon implantation. Non-limiting examples of suitable bioremodelable materials include reconstituted or naturally-derived collagenous materials. Suitable collagenous materials may include an extracellular matrix material (ECM) that possesses biotropic properties, such as submucosa, renal capsule membrane, dermal collagen, dura mater, pericardium, fascia lata, serosa, peritoneum or basement membrane layers. Suitable submucosa materials may include, for example, intestinal submucosa, including small intestinal submucosa (SIS), stomach submucosa, urinary bladder submucosa, and uterine submucosa. One non-limiting example of a suitable remodelable material is the SURGISIS® BIODESIGN™, commercially available from Cook Incorporated, Bloomington, Ind. Another suitable remodelable material is the graft prosthesis material described in U.S. Pat. No. 6,206,931, which is incorporated herein by reference in its entirety.

The prosthesis described herein can also include a coating of one or more therapeutic agents along a portion of the conduit body and/or the graft coverings. Therapeutic agents for use as biocompatible coatings are well known in the art. Non-limiting examples of suitable bio-active agents that may be applied to the prosthesis include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Those skilled in the art will appreciate that other bioactive agents may be applied for a particular use. The bioactive agent can be incorporated into, or otherwise applied to, portions of the prosthesis by any suitable method that permits adequate retention of the agent material and the effectiveness thereof for its intended purpose.

Figure 5:
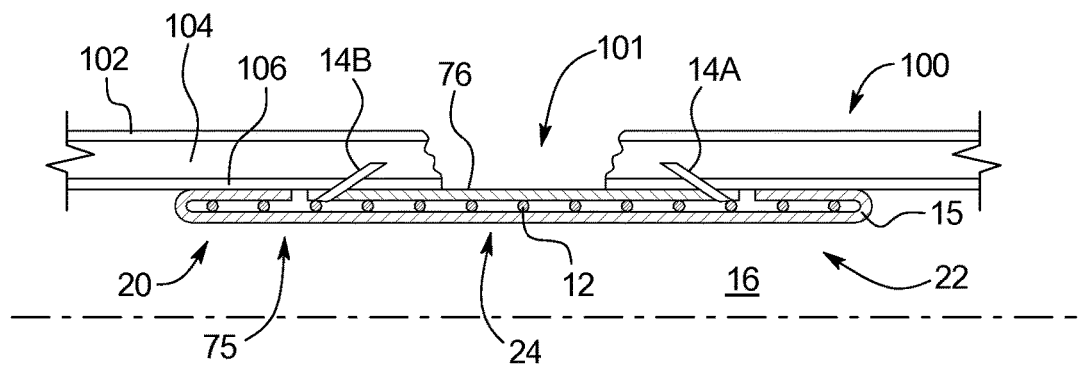
FIG. 5 is a partial elevation cross-sectional view depicting a deployed vascular conduit according to one of the described embodiments, engaged with a body vessel.

FIG. 5 illustrates a prosthesis (75) engaging with the body vessel (100) with a laceration (101) through a wall of the vessel. The components in this figure are exaggerated in order to better illustrate the implantation. Conduit (75) includes the first and second series of barbs (14A & 14B), with the barbs shown penetrating the tunica intima (106) and into the tunica media (104), and avoiding penetration of the tunica adventitia (102). Graft covering (15) is shown extending along the luminal wall of the conduit and everted around the ends of the conduit to extend to the respective gaps. As shown, the proximal and distal portions (20,22) of conduit body (12) with graft covering (15) along the exterior surface can sealably engage with the vessel wall of body vessel (100) to prevent any leakage of blood for gaining hemostasis and to force blood to flow within lumen (16) of the prosthesis for enhancing blood perfusion. Also shown is the intermediate portion of a prosthesis with covering (76) sealing the edges of laceration (101).

As can be appreciated from the above disclosure, the prosthesis disclosed herein may comprise a self-expanding stent having barbs near each end of the stent and a graft layer (graft covering) to prevent fluid flow out of the walls of the stent. Additionally, the prosthesis may comprise one or more sleeves that can be used in a system for delivering the prosthesis to a target location. For example, a sleeve may be wrapped around the prosthesis such that the stent is held in a radially compressed configuration. When the prosthesis is inserted at the desired location during an open surgical procedure, the sleeve may be removed thereby allowing the stent to expand and causing the barbs on each end of the graft to engage an inside surface of the target location, such as a transected or lacerated artery or vein.

The sleeve may be made of any material that is biocompatible and suitable to retain the prosthesis, or one or more portions of the prosthesis, in a radially compressed configuration, and yet still capable of being removed from the prosthesis to allow radial expansion of the covered portion(s) of the prosthesis. In some embodiments, the sleeve comprises a water or liquid dissolvable material with a rate of dissolution of about 1 to about 20 seconds, such as about 5 to about 10 seconds. In some embodiments, if it is desirable for the sleeve to dissolve at a slower rate, the sleeve may comprise a rate of dissolution of about 30 seconds to about 5 minutes. One of ordinary skill in the art will understand how to produce a sleeve having a slower rate of dissolution, such as by introducing crosslinks into the sleeve with an appropriate crosslinking agent. In one embodiment, any of the sleeves disclosed herein may comprise hydroxypropyl methylcellulose (HPMC). HPMC hydrogels containing polyethylene glycol (PEG) crosslinks may be prepared by reacting HPMC sodium salt with PEG dichloride, for example.

Sleeves comprising HPMC have certain advantages that impart beneficial characteristics to the presently disclosed prosthesis. For example, when enough of the HPMC dissolves such that the radial force of the underlying prosthesis overcomes the strength of the sleeve, the prosthesis will expand and engage the vessel wall. However, in certain embodiments, any remaining HPMC that has not yet dissolved will also engage the vessel wall and before it dissolves, it will create a temporary seal between the prosthesis and the vessel wall.

In this regard, the present disclosure also relates to any self-expanding structure comprising a HPMC sleeve. One or more HPMC sleeves may be disposed around the outside of an annular space of any self-expanding coated/grafted structure such that when the sleeve is exposed to an activating agent, such as a liquid (e.g. water or blood), a portion of the sleeve dissolves, thereby allowing the HPMC covered portion to expand and engage a surrounding body, such as a vessel, and any remaining, undissolved HPMC, forms a temporary seal between the surrounding body and the expanded structure. Such a device may be used, for example, in a method for sealing a connection between a self-expanding structure and a surrounding body. The sleeve may be configured such that the seal lasts for any desired amount of time, such as between about 3 seconds and about 1 week. As noted above, one of ordinary skill in the art will understand how to produce a sleeve having a given rate of dissolution.

The inventors have also discovered that a sleeve comprising HPMC coupled with a prosthesis comprising nitinol has additional advantages. For example, HPMC may dissolve at different rates depending upon the temperature of the activating agent. If a low temperature activating agent is used, such as cold water, the HPMC may dissolve at a slower rate than if hot water is used. Further, nitinol is a material that has superelastic properties. It undergoes a phase transformation in its crystal structure when its cooled from the stronger, high temperature form (Austenite) to the weaker, low temperature form (Martensite). As such, when a higher temperature activating agent is used, such as blood, to dissolve the HPMC, not only does the HPMC dissolve faster, the nitinol strengthens thereby exerting a higher radial force on the sleeve to allow for a faster expansion of the prosthesis. In turn, when the prosthesis is in its compressed configuration within the sleeve before being exposed to a high temperature activating agent, it is less rigid and exerts less radial force on the HPMC sleeve, thereby preventing premature expansion.

The sleeve may have a uniform wall thickness or the sleeve may have a wall thickness that varies along its length. For example, the sleeve may have a distal end, a middle portion, and a proximal end, wherein a wall thickness of the distal end is thinner than a wall thickness of the proximal end. In such an embodiment, the sleeve comprises a tapered configuration and may resemble a cone, for example. A conical-shaped sleeve, having the point of the cone or smaller diameter portion of the cone at the distal end of the sleeve will help to guide the sleeve into a vessel or surrounding body. The taper may be gradual from the proximal end to the distal end or the taper may comprise a step, whereby a proximal portion of the sleeve comprises a given wall thickness, the distal portion of the sleeve comprises a thinner wall thickness than the proximal portion, and a mid-section of the sleeve comprises a step where the wall thickness changes. Alternatively, the sleeve may have a distal end, a middle portion, and a proximal end, wherein a wall thickness of the proximal end is thinner than a wall thickness of the distal end. In one embodiment, a sleeve having a distal end comprising a thinner wall thickness and a proximal end comprising a thicker wall thickness may be disposed on a distal end of a prosthesis. Optionally, a sleeve having a proximal end comprising a thinner wall thickness and a distal end comprising a thicker wall thickness may be disposed on a proximal end of a prosthesis. The middle portion of the prosthesis may remain uncovered by the sleeves and thus, the middle portion of the prosthesis may be in an expanded configuration while the portions of the prosthesis that are covered by the sleeves may be in radially compressed configurations.

In some embodiments, the sleeve is removed from the prosthesis using an activating agent. For example, the activating agent may dissolve the sleeve. Exposure of the sleeve to the activating agent causes the sleeve to dissolve and thereby allows the portion of the prosthesis formerly covered by the sleeve to expand to its original, uncompressed diameter. It follows that a thinner sleeve or a thinner portion of a sleeve will generally dissolve faster than a thicker sleeve or thicker portion of a sleeve. For example, if the entire sleeve is manufactured from the same material, such as HPMC, and some portions have thinner wall thicknesses than others, the portions having the thinner wall thicknesses will dissolve faster, upon exposure to an activating agent, than the portions having thicker wall thicknesses.

Figure 7A:
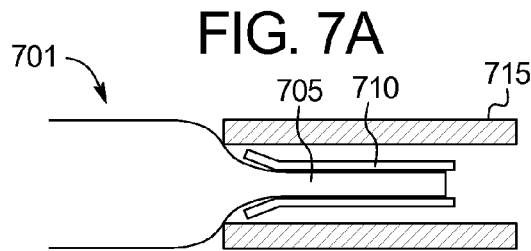
FIGS. 7A and 7B schematically depict deployment of a prosthesis.
Figure 7B:
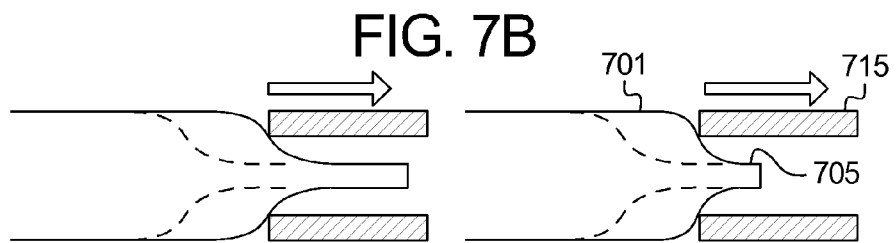

There are problems known in the art with respect to deployment of grafts using a single, dissolvable sleeve that has a uniform wall thickness. For example, FIG. 7A illustrates a prosthesis according to one embodiment of the present disclosure. The prosthesis comprises a self-expanding stent and a dissolvable sleeve. The self-expanding stent is in both a compressed state (705) and an expanded state (701). The sleeve (710) is shown having a uniform wall thickness and is disposed on the compressed portion (705) of the self-expanding stent. Due to the already existing stress on the proximal end of the sleeve by the underlying expanding stent, the sleeve tends to split or open in a proximal to distal direction. If the sleeve and vessel (715) are not held in position, the expansion of the stent in the proximal to distal direction can exert an axial force on the end of the vessel, either causing the vessel to slide off of the graft or causing the graft to slide out of the vessel before the barbs can engage the vessel. This can be seen in FIG. 7B, where, as compared to FIG. 7A, the distal end of the stent has moved proximally within the lumen of the artery because expansion of the stent occurred in a proximal to distal direction.

However, the present disclosure addresses such a problem by providing: 1) a first sleeve having a defined wall thickness and a second sleeve having a thinner or a thicker wall thickness than the first sleeve, wherein the sleeves are placed adjacent one another, in series, on a proximal and/or distal end of the graft; 2) a first sleeve having a defined wall thickness and an additional sleeve overlapping a portion of the first sleeve, wherein the portion of the first sleeve having the additional sleeve disposed thereon comprises a thicker wall thickness than the portion of the first sleeve that is not covered by the additional sleeve; or 3) a sleeve that has a thinner wall thickness at one of its ends and a thicker wall thickness at the opposite end.

Figure 8A:
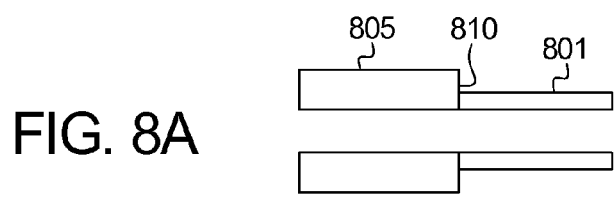
FIG. 8A depicts an embodiment of a sleeve according to the present disclosure.
Figure 8B:
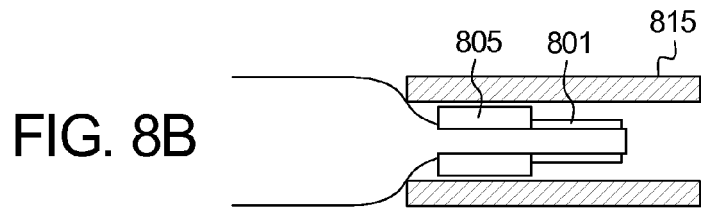
FIGS. 8B-8D schematically depict deployment of a prosthesis comprising the sleeve of FIG. 8A.

When referring to sleeves placed in series, it should be understood that the sleeves are placed next to each other along the longitudinal axis of the prosthesis, as depicted in FIGS. 8A and 8B. For example, a first sleeve (805) comprises a proximal and distal end. A second sleeve (801) comprises a proximal and distal end. If the first and second sleeves are placed in series at a distal end of the prosthesis, the first sleeve (805) would be guided over the distal end of the prosthesis and advanced in a proximal direction to cover a portion of the distal end but also allow a distal-most portion of the distal end to remain uncovered. Then, the second sleeve (801) may be guided over the distal end of the prosthesis until its proximal end abuts the distal end of the first sleeve (805). Preferably, the distal end of the second sleeve (801) covers or substantially covers the distal-most end of the prosthesis. Thereby, the second sleeve (801) is located distally adjacent the first sleeve (805), in series, along a length of the distal end of the prosthesis. Alternatively, each sleeve may be applied to the prosthesis or stent by drip coating the sleeve material onto the prosthesis or stent.

If the sleeve comprises a thinner wall thickness at its distal end and a thicker wall thickness at its proximal end and an activation agent is applied generally to the sleeve, the distal end of the sleeve will dissolve first, thereby allowing the distal end of the underlying graft to open before the portion of the graft which is covered by the proximal end of the sleeve.

In some embodiments, the middle portion of the prosthesis does not comprise a sleeve (it remains uncovered by a sleeve) and instead, a sleeve (or a plurality of sleeves) is only disposed on a proximal and/or distal end of the prosthesis. In other embodiments, the middle portion of the graft does not comprise a sleeve (it remains uncovered by a sleeve) but the proximal end of the graft comprises a first sleeve and the distal end of the graft comprises a second sleeve. The first and second sleeves may have uniform wall thicknesses or the wall thickness of the first and second sleeves may vary. For example, the first sleeve disposed on the proximal end of the graft may have a thinner wall thickness at its proximal end than at its distal end. In some embodiments, the proximal end of the first sleeve may have the thinnest wall thickness and the thickness of the wall of the sleeve may gradually increase moving distally along the sleeve such that the distal end of the first sleeve has the largest wall thickness. Moreover, the second sleeve disposed on the distal end of the graft may have a thinner wall thickness at its distal end than at its proximal end. In some embodiments, the distal end of the second sleeve may have the thinnest wall thickness and the thickness of the wall of the sleeve may gradually increase moving proximally along the sleeve such that the proximal end of the second sleeve has the largest wall thickness.

FIG. 8A shows a first sleeve (805) having a thicker wall thickness than a second sleeve (801). In the specific example shown in FIGS. 8A and 8B, there is an abrupt step or increase in outer diameter/wall thickness when moving from the proximal end of the second sleeve (801) to the distal end of the first sleeve (805). However, as opposed to having a step-wise configuration, the wall thickness/outer diameter of each sleeve may also gradually increase or decrease.

Figure 8C:
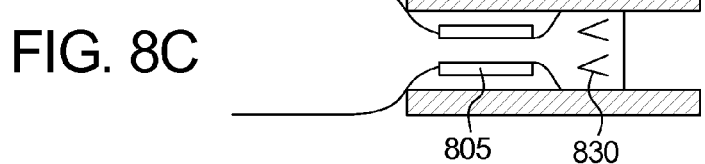
Figure 8D:
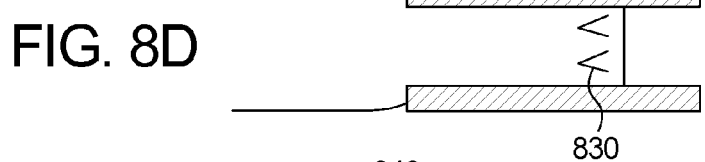

FIG. 8B shows the prosthesis inserted into the lumen of a vessel (815), such as an artery or vein. The prosthesis comprises a first sleeve (805) and the first sleeve (805) has a thicker wall thickness than a second sleeve (801) placed in series on the prosthesis. When the sleeves are exposed by an activating agent, the sleeves may begin to dissolve and may eventually dissolve entirely. As shown in FIG. 8C, second sleeve (801) dissolved before first sleeve (805) since second sleeve (801) had a thinner wall thickness than first sleeve (805). Since second sleeve (801) dissolved, the distal-most end of the prosthesis expanded, because it was no longer covered by second sleeve (801), and anchored to an inner portion of the lumen of the vessel using barbs (830). Upon continued exposure to the activating agent, first sleeve (805) eventually dissolves, thereby allowing the remainder of the distal end of the prosthesis to expand, as shown in FIG. 8D. Such a configuration is particularly advantageous in that it allows the distal-most portion of the prosthesis to expand first, thereby allowing the graft to anchor itself to the vessel and subsequently, when the remainder of the prosthesis expands, it does not cause the prosthesis to retract in a proximal direction from the lumen of the vessel. In some embodiments, the barbs are preferably covered by the sleeve having the thinner wall thickness and the sleeve having the thicker wall thickness covers a non-barbed section of the stent located inward from the barbs.

Figure 9:
FIG. 9 depicts an embodiment of a sleeve configuration according to the present disclosure.

In some embodiments, the first sleeve may not be present, as shown in FIG. 9, but an additional sleeve (940) may be used to overlap a portion of the second sleeve (901). The additional sleeve may simply be placed over the second sleeve. It may be bonded to the second sleeve or it may not be bonded to the second sleeve. In view of FIGS. 8B-8D, it can be envisioned that when an additional sleeve is used to overlap a proximal portion of a second sleeve, upon exposure to an activating agent, the distal portion of the second sleeve, which is uncovered by the additional sleeve, will dissolve first, thereby allowing the underlying graft portion to expand first. Upon continued exposure to the activating agent, the additional sleeve will dissolve, thereby exposing the covered portion of the second sleeve, which will subsequently dissolve, thereby allowing the portion of the graft covered by the additional sleeve and the second sleeve to expand.

While FIGS. 8A-8D depict configurations where a distal end of a prosthesis is inserted into a vessel, it should be understood that a proximal end of the prosthesis may also be inserted into a vessel and the proximal end may include first and second sleeves similar to the sleeves described above, except that the second sleeve (sleeve located at the proximal-most end of the prosthesis) would have a thinner wall thickness than a first sleeve located distally adjacent the second sleeve, so the proximal-most end of the prosthesis would expand first.

The same is also true with respect to the overlapping sleeves shown in FIG. 9. If the configuration of sleeves shown in FIG. 9 was placed at a proximal end of a prosthesis, a configuration of sleeves as in FIG. 9 could also be placed at the proximal end of the prosthesis except the proximal portion of the second sleeve would remain uncovered by the additional sleeve while the distal end of the second sleeve would be covered by the additional sleeve.

In some embodiments, the prosthesis comprises a proximal end, a middle portion, and a distal end. The proximal end may comprise anywhere from about 1% to about 40% of a proximal portion of the prosthesis and the distal end may comprise anywhere from about 1% to about 40% of the distal end of the prosthesis. For example, the proximal end of the prosthesis may comprise a portion of the prosthesis beginning at its proximal-most end and extending distally along the prosthesis to about 10%, or about 15%, or about 20%, or about 25%, or about 30%, or about 35%, or about 40% of its total length. The distal end of the prosthesis may comprise a portion of the prosthesis beginning at its distal-most end and extending proximally along the prosthesis to about 10%, or about 15%, or about 20%, or about 25%, or about 30%, or about 35%, or about 40% of its total length.

As an illustrative example, a prosthesis may comprise a length of about 9 cm. Moving distally along the prosthesis, the proximal end may comprise the first 1 cm length of the prosthesis, the first 2 cm length of the prosthesis, the first 3 cm length of the prosthesis, the first 4 cm length of the prosthesis, or any length therebetween, such as the first 1.5 cm, 2.5 cm, 3.5 cm, etc. The distal end of the prosthesis may comprise the last 1 cm length of the prosthesis, the last 2 cm length of the prosthesis, the last 3 cm length of the prosthesis, the last 4 cm length of the prosthesis, or any length therebetween, such as the last 1.5 cm, 2.5 cm, 3.5 cm, etc.

If a sleeve comprises an end having a thinner wall thickness and an end comprising a thicker wall thickness, the end comprising the thicker wall thickness may comprise from about 25% to about 60% of the total length of the sleeve and the end comprising the thinner wall thickness may comprise from about 40% to about 75% of the total length of the sleeve. In some embodiments, the end comprising the thicker wall thickness may comprise from about 33% to about 50% of the total length of the sleeve and the end comprising the thinner wall thickness may comprise from about 50% to about 67% of the total length of the sleeve.

If a prosthesis comprises a first sleeve on its proximal-most end and a second sleeve located distally adjacent the first sleeve, then the length of the first and second sleeves may be added together to obtain a total length. The first sleeve may have a thinner wall thickness than the second sleeve. In view of the total length of both of the sleeves added together, the second sleeve may comprise from about 25% to about 60% of the total length and the first sleeve may comprise from about 40% to about 75% of the total length. In some embodiments, the second sleeve may comprise from about 33% to about 50% of the total length and the first sleeve may comprise from about 50% to about 67% of the total length of the first and second sleeves.

Any of the sleeves disclosed herein can have sizes configured by one of ordinary skill ion the art depending upon the desired application of the prosthesis, the size of the target vessel, etc. In some embodiments, a sleeve may have an outer diameter from about 2.5 mm to about 9 mm. For example, the outer diameter of a sleeve may be from about 4 mm to about 8 mm. The wall thickness of a sleeve may be between about 0.25 mm and about 2.5 mm. For example, the thickness may be between about 0.65 mm and about 2.35 mm.

If the sleeve comprises a portion having a thinner wall thickness and a portion comprising a thicker wall thickness, and the portion comprising the thicker wall thickness has an outer diameter from about 2.5 mm to about 9 mm and a wall thickness from about 0.25 mm to about 2.5 mm, then the portion of the sleeve comprising the thinner wall thickness may have an outer diameter from about 2.23 mm to about 7 mm and a wall thickness from about 0.115 mm to about 1.5 mm, provided that the wall thickness and outer diameter of the portion having the thinner wall thickness are smaller than the wall thickness and outer diameter of the portion having the thicker wall thickness. In some embodiments, the portion of the sleeve having the thinner wall thickness may have an outer diameter from about 2.9 mm to about 5.3 mm and a thickness from about 0.117 mm to about 1 mm.

The portion having the thicker wall thickness may be formed during manufacture of the sleeve or a first sleeve may be provided and an additional sleeve may be disposed on either a proximal or distal end of the first sleeve, thereby creating a thicker wall thickness on the portion of the first sleeve overlapped by the additional sleeve.

If two or more sleeves are disposed adjacent one another, in series, on a proximal and/or distal end of the prosthesis, each sleeve may have a substantially uniform outer diameter and wall thickness, provided that each sleeve has a different outer diameter and wall thickness as compared to the other sleeves. For example, if a first sleeve is disposed on the distal-most end of the prosthesis and a second sleeve is placed proximally adjacent the first sleeve, in series, then the first and second sleeves may have different wall thicknesses and outer diameters. For example, the first sleeve may comprise an outer diameter from about 2.23 mm to about 7 mm and a wall thickness from about 0.115 mm to about 1.5 mm, provided that the wall thickness and outer diameter of the first sleeve are smaller than the second sleeve. The second sleeve may have an outer diameter from about 2.5 mm to about 9 mm and a wall thickness between about 0.25 mm and about 2.5 mm, provided that the wall thickness and outer diameter of the second sleeve are larger than the first sleeve.

In one illustrative embodiment, a prosthesis may comprise a first sleeve located at its distal-most end, a second sleeve located proximally adjacent the first sleeve, in series, on the distal end of the prosthesis, a third sleeve located at its proximal-most end, and a fourth sleeve located distally adjacent the third sleeve, in series, on the proximal end of the prosthesis. The middle portion of the prosthesis remains uncovered by the sleeves and may be in an expanded configuration while the portions of the prosthesis covered by the sleeves may be in a radially compressed configuration. The first and third sleeves may have outer diameters of about 3.5 mm and wall thicknesses of about 0.2 mm. The second and fourth sleeves may have outer diameters of about 5 mm and wall thicknesses of about 1 mm.

When comparing a sleeve having a thinner end and a thicker end, one may select certain wall thickness ratios that may be advantageous. For example, a ratio of the wall thickness of the thicker end to the wall thickness of the thinner end may be from about 1.2:1 to about 4:1, or from about 2:1 to about 3:1. Similarly, if two sleeves are placed in series along a proximal end of the prosthesis, the wall thickness ratio of the distal sleeve to the proximal sleeve may be from about 1.2:1 to about 4:1, such as from about 2:1 to about 3:1. Moreover, if two sleeves are placed in series along a distal end of the prosthesis, the wall thickness ratio of the proximal sleeve to the distal sleeve may be from about 1.2:1 to about 4:1, such as from about 2:1 to about 3:1.

In any of the embodiments disclosed herein, the prosthesis may comprise one or more caps and/or one or more tubes. For example, if the prosthesis comprises a sleeve at its proximal end, it may also comprise a tube located proximally adjacent the sleeve. Additionally, a cap may be disposed around the sleeve and the cap. Such a configuration is illustrated in FIG. 11.

Figure 11:
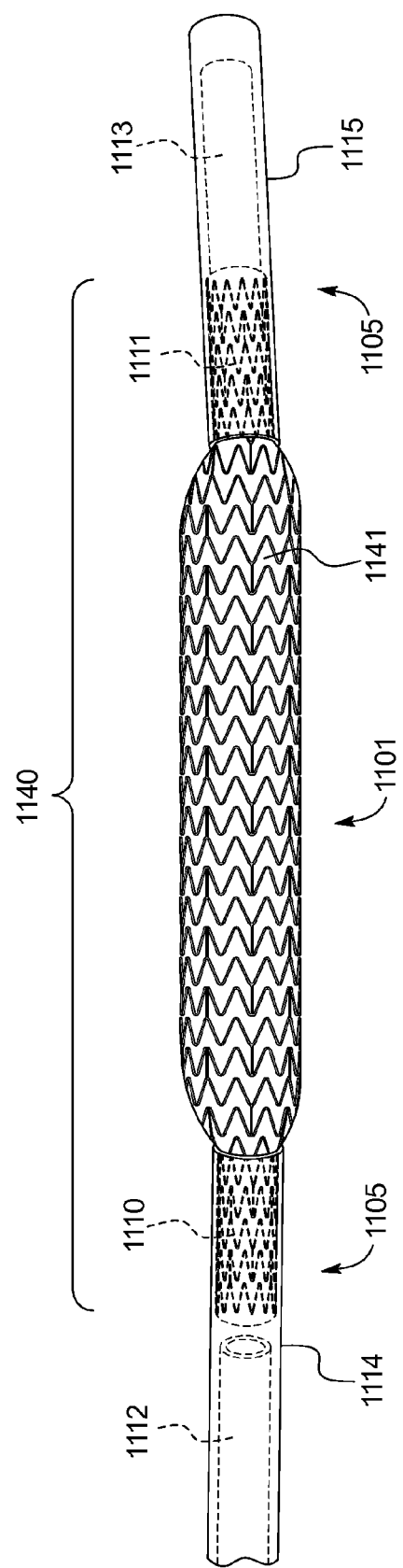
FIG. 11 depicts an embodiment of a prosthesis according to the present disclosure.

FIG. 11 depicts a self-expanding stent (1140) comprising an expanded portion (1101) and two compressed portions (1105). The stent (1140) also comprises a graft covering (1141). A proximal end of the stent (1140) comprises a first sleeve (1110) and a first tube (1112) located proximally adjacent the first sleeve (1110). A first cap (1114) is disposed around the first sleeve (1110) and the first tube (1112). The distal end of the stent (1140) comprises a similar configuration. As can be seen, the distal end comprises a second sleeve (1111) and a second tube (1113) located distally adjacent the second sleeve (1111). A second cap (1115) may be disposed around the second sleeve (1111) and the second tube (1113).

The sleeves (1110,1111) may comprise any desirable wall thicknesses as previously discussed above. For example, the first sleeve may comprise a variable wall thickness wherein the proximal end comprises a thinner wall thickness than the distal end. The second sleeve may comprise a thinner wall thickness at its distal end and a thicker wall thickness at its proximal end. Other sleeve configurations may be used in connection with the tubes and caps as well. For example, instead of having one sleeve at the proximal end and one sleeve at the distal end of the stent, there may be two sleeves, placed in series, at each end, as previously discussed above. The inner diameter of the caps may be configured by one of ordinary skill in the art depending upon the outer diameter(s) of the one or more sleeves.

For example, if a sleeve has a smaller outer diameter at its distal end and a larger outer diameter at its proximal end, then the cap disposed around this sleeve may have a smaller inner diameter at its distal end and a larger inner diameter at its proximal end. Additionally, if two sleeves are placed in series on an end of the prosthesis, the cap to be disposed around these sleeves may have its inner diameter configured to be very slightly larger than the outer diameter(s) of each sleeve.

In FIG. 11, the distal end of the first tube (1112) is proximally adjacent the proximal end of the first sleeve (1110). However, in some embodiments, the distal end of the first tube (1112) may extend into a lumen of the first sleeve (1110) and in certain embodiments, the distal end of the first tube (1112) may extend into the lumen of the first sleeve (1110) and past the distal end of the first sleeve (1110). The same holds true at the distal end of the stent (1140). The proximal end of the second tube (1113) may extend into a lumen of the second sleeve (1111) and in certain embodiments, the proximal end of the second tube (1113) may extend into the lumen of the second sleeve (1111) and past the proximal end of the second sleeve (1111).

The tubes and caps may be made from any suitable materials, such as plastics, metals, polymers, etc. In some embodiments, the tubes may comprise polyethylene and the caps may comprise Teflon™. In other embodiments, the tubes and caps may comprise one or more materials selected from polyurethane, Nylon, polypropylene, and fluorinated ethylene propylene. The caps assist in holding the sleeves and tubes in place until the device is ready to be implanted. In one embodiment, the second cap (1115) and the second tube (1113) may be removed and the distal end of the prosthesis may be placed within an end of a transected vessel. An activating agent is applied to the distal end of the prosthesis, thereby causing second sleeve (1111) to dissolve, thereby allowing the distal end of the stent to expand and engage an inner wall of the vessel. If any fluid were to travel through the prosthesis at this time and exit the proximal end, the first sleeve (1110) would be protected from the fluid by the first tube (1112), especially if the first tube (1112) extends into a lumen of the first sleeve (1110).

Next, the first cap (1114) and the first tube (1112) may be removed. The proximal end of the prosthesis may then be placed into the lumen of the opposite end of the transected vessel. An activating agent may then be applied to the first sleeve (1110) to cause the first sleeve (1110) to dissolve, thereby allowing the proximal end of the prosthesis to expand and engage the inner wall of the transected vessel. Once both ends of the prosthesis engage the transected vessel, blood flow can resume through the transected vessel/prosthesis.

Figure 6A:
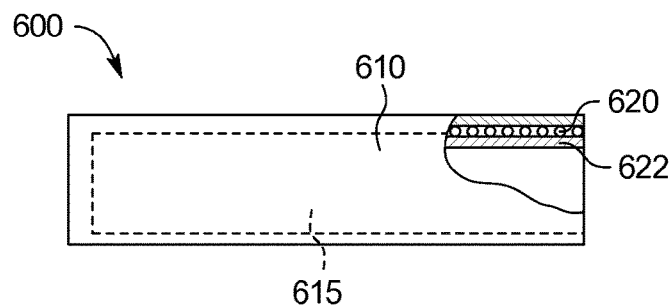
FIG. 6A is an elevation view of an embodiment of a delivery system for deploying a prosthesis, depicting a removable sleeve that can dissolve.

FIGS. 6A-6E illustrate a system (600) and a delivery method for a prosthesis according to certain embodiments of the present disclosure. FIG. 6A depicts the system (600) including a prosthesis (615) retained in a radially compressed configuration within a removable sleeve (610). Although the sleeve is disposed on/around the entire length of the prosthesis in these figures, it should be understood that the entire length of the prosthesis need not comprise or be covered by the sleeve. For example, only the proximal end of the prosthesis may be covered by the sleeve, only the distal end of the prosthesis may be covered by the sleeve, or both of the proximal and distal ends of the prosthesis may be covered by the sleeve, while a middle portion of the prosthesis remains uncovered by the sleeve. Additionally, the distal end of the prosthesis may be covered by a first and second sleeve placed in series and the proximal end may be covered by a third and fourth sleeve placed in series. The middle portion will usually be in its radially expanded configuration but during delivery of the prosthesis, the middle portion may be radially compressed because it is being pinched by the fingers of a physician or by forceps, for example, during delivery.

A partial cutaway of FIG. 6A shows the various layers of the prosthesis (615), such as a support structure (620) and a graft body (622) in relation to the sleeve (610). To remove the sleeve, the sleeve (610) can be configured to rapidly weaken, and, dissolve in some embodiments, in response to application of an activating agent (630). In other words, the sleeve (610) can be weakened to a degree where the radial expansion forces of the prosthesis can overcome the retaining forces of the sleeve, thereby allowing the prosthesis to move to the radially expanded configuration. Thereafter, if desirable, the (610) sleeve may continue to dissolve in its entirety.

Examples of activating agents (630) may include any type of moisture, such as blood or saline, which is commonly found in the emergency room setting. Materials of the sleeve (610) that dissolve once interfaced with saline include: pullulan, which is an extracellular bacterial polysaccharide produced from starch by *Aureobasidium pullulans*; HPMC; non animal-derived film-forming polymers, for example, polyvinyl alcohol, plant-derived film-forming polymers such as starch, starch derivatives, cellulose, cellulose derivatives other than HPMC, and mixtures thereof; bacterial-derived film-forming polymers such as exo-polysaccharides like xanthan, acetan, gellan, welan, rhamsan, furcelleran, succinoglycan, scleroglycan, schizophyllan, tamarind gum, curdlan, dextran and mixtures thereof; and gelling systems including one or more cations and/or one or more gelling agents, with cations such as $K^+$, $Na^+$, $Li^+$, $NH_4^+$, $Ca^{++}$, $Mg^{++}$ and mixtures thereof, and gelling agent(s) such as hydrocolloids such as alginates, agar gum, guar gum, locust bean gum (carob), carrageenans, tara gum, gum arabic, ghatti gum, khaya grandifolia gum, tragacanth gum, karaya gum, pectin, arabian (araban), xanthan, gellan gum, konjac mannan, galactomannan, funoran, and mixtures thereof.

It can be appreciated by those skilled in the art that other activation agents and corresponding sleeve materials can be selected to perform the same function. Other examples include poly ethylene glycol, poly ethylene oxide, poly vinylpyrrolidone, a glycosaminoglycan, polysaccharides, polysaccharide derivatives, poly hyaluronic acid, poly alginic acid, chitin, chitosan, chitosan derivatives, hydroxyethyl cellulose, hydroxypropyl cellulose, carboxymethyl cellulose, poly peptides, poly lysine, poly glutamic acid, and proteins, such as albumin.

In one example, a polysaccharide may include tamarind gum (such as xyloglucan polymers), guar gum, chitosan, chitosan derivatives, locust bean gum (such as galactomannan polymers), and other industrial gums and polymers, which include, but are not limited to, Tara, Fenugreek, Aloe, Chia, Flaxseed, Psyllium seed, quince seed, xanthan, gellan, welan, rhamsan, dextran, curdlan, pullulan, scleroglucan, schizophyllan, chitin, hydroxyalkyl cellulose, arabinan (such as sugar beets), de-branched arabinan (such as from sugar beets), arabinoxylan (such as rye and wheat flour), galactan (such as from lupin and potatoes), pectic galactan (such as from potatoes), galactomannan (such as from carob, and including both low and high viscosities), glucomannan, lichenan (such as from icelandic moss), mannan (such as ivory nuts), pachyman, rhamnogalacturonan, acacia gum, agar, alginates, carrageenan, chitosan, clavan, hyaluronic acid, heparin, inulin, cellodextrins, and mixtures thereof.

Polymers can be crosslinked to improve strength of sleeve and/or solubitliy of sleeve. Such crosslinking of polymers is described in U.S. Pat. No. 7,960,453, which is incorporated herein by reference in its entirety. While any water-soluble material, such as cellulosic materials, gums, polymers, starches, proteins, and combinations thereof can be used, an example sleeve is made of glucans because of its high water solubility and rapid dissolution. Examples of glucans include pullulan and elsinan. It can be appreciated by those skilled in the art that other activation agents and corresponding sleeve materials can be selected to perform the same function.

The sleeve can be made by any process known in the art. For example, a solution of the desired sleeve material can be prepared in a water or saline solution. A mandrel can be dipped into the solution to form a dip coating on the mandrel. It is recognized that the sleeve material may be applied by other means to coat the mandrel. The coated mandrel can be dried in air to form the sleeve. In some embodiments, the sleeve may comprise materials are thermoformable and can be extruded into a tubular segment. In other embodiments, the sleeve may comprise a material that can be formed in a sheet, which may have a square or rectangular shape, for example. One of the edges of the sheet may be dampened using a small quantity of water and then joined/bonded to the opposite edge of the sheet to form a tubular sleeve. One of ordinary skill in the art will understand how to use any of these techniques to form a sleeve with varying wall thicknesses, such as a sleeve comprising a proximal end that has a thinner wall thickness than its distal end. A portion of the prosthesis, such as its distal end, may be radially compressed with a stent compressor or by other known means in the art. The compressed portion of the prosthesis can be transferred to within the lumen of the sleeve. Alternatively or additionally, a proximal end of the prosthesis may be radially compressed and transferred to within the lumen of a second sleeve.

Figure 6B:
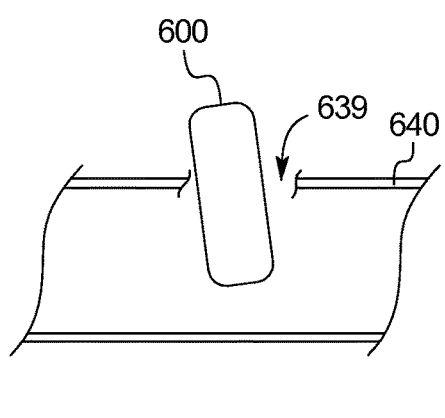
FIGS. 6B-6E are partial elevation cross-sectional views of a damaged body vessel, depicting alternative method steps of deploying a prosthesis using the system of FIG. 6A.
Figure 6C:
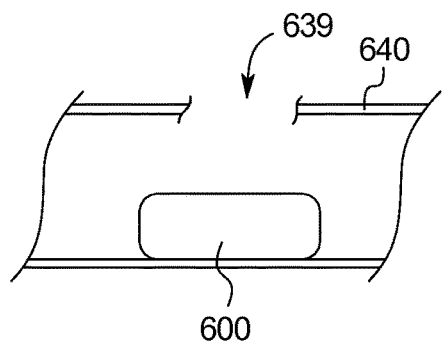
Figure 6D:
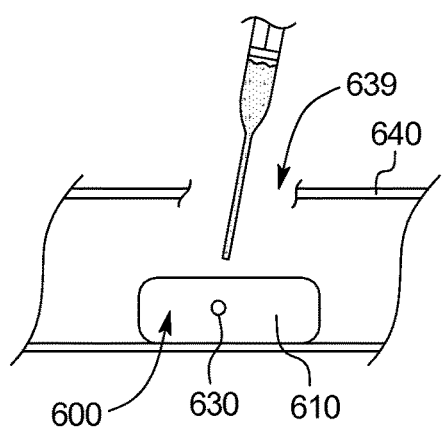
Figure 6E:
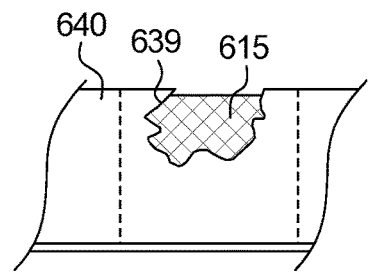

The system (600) can be inserted manually through a laceration (639) of a body vessel (640), as shown in FIG. 6B, and then repositioned to be substantially centered over the laceration, as shown in FIG. 6C. The activating agent (630) can be applied to the sleeve (610) in order to begin the weakening or dissolving process. FIG. 6D shows the use of a syringe suitably pressurized to release a sufficient amount of the activating agent (630) to rapidly weaken or dissolve the sleeve (610). The time to weaken or dissolve the sleeve (610) can depend on the material and concentration of the sleeve and the activating agent, but it is desirable that the total time be as quick as possible, e.g., less than about 5 to 10 seconds for a sleeve having a thinner wall thickness and less than about 8 to about 13 seconds for the sleeve having the thicker wall thickness. FIG. 6E shows the prosthesis (615) in the radially expanded configuration engaged with the body vessel (640) after the sleeve (610) has dissolved, sealing the laceration (639) from within or interconnecting the two vessel portions, in order to gain hemostasis or fluid stability and still allow blood perfusion or fluid flow.

Figure 10A:
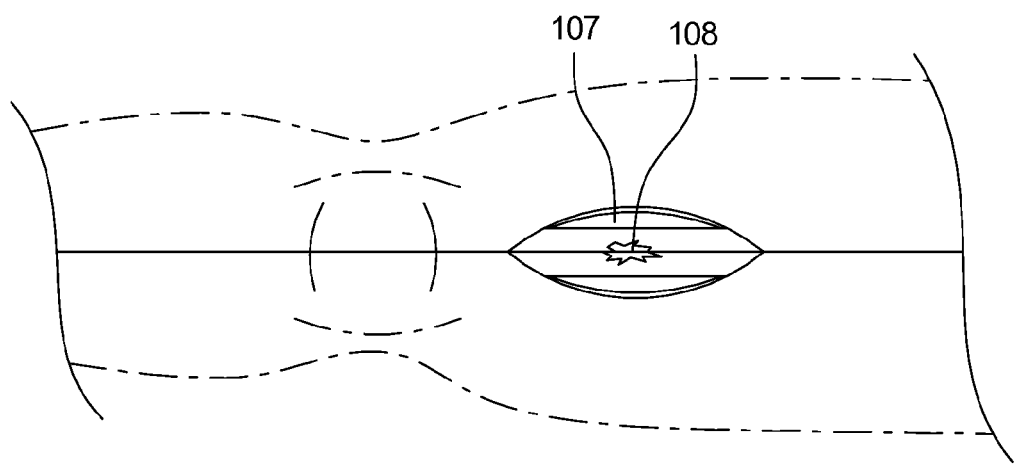
FIGS. 10A-10B illustrate a method of open surgical repair of a body vessel with a delivery system deploying a prosthesis.
Figure 10B:
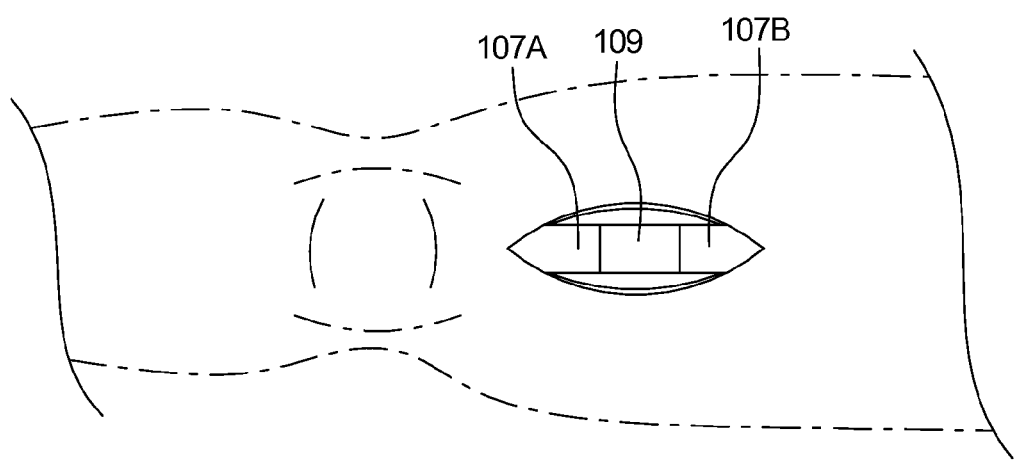

Further appreciation of the presently disclosed prosthesis and delivery system can be gained with reference to FIGS. 10A-10B. FIG. 10A depicts an example body vessel (107), such as one found in the leg of a patient. The body vessel (107) has previously been subjected to a traumatic episode, resulting in a portion (108) of body vessel (107) being torn away or otherwise severely damaged. Pre-surgery preparation has been applied to the leg and a trauma pathway may be formed therein in order to gain access to the body vessel and the damaged portion thereof through an open surgical procedure. After clamping the body vessel (107) on both ends of the portion (108) to restrict blood flow temporarily, the body vessel (107) can be cut or transected by the clinician into two portions (see 107A and 107B in FIG. 10B). In one example, the lacerated portion (108) remains without requiring transection and the opening formed thereby can be used for insertion of the prosthesis. The transection may be at the damaged portion (108) of the blood vessel (107) or as far away as necessary from the damaged portion to remove unhealthy portions of the body vessel or unrepairable portions of the body vessel. Sutures can be attached to the end openings of the body vessel portions (107A, 107B) to keep them fixed in place and opened to facilitate insertion of the prosthesis. Forceps may also be used in a similar manner. Any number of sutures can be used to retain the end openings in the open position, although triangulation sutures can be sufficient, with each suture being about 120 degrees apart from the adjacent suture.

A prosthesis is selected to have a radial expanded cross-section and a longitudinal length sufficient to bridge the laceration in the vessel or the gap between the body vessel portions (107A, 107B) and radially fit within the body vessel portions.

In some embodiments, the prosthesis may be inserted into the body through the trauma pathway and positioned at the body vessel. In certain embodiments, the vessel is transected and in others, the vessel is lacerated. If the vessel is lacerated, the physician may manually sever the vessel to form a transected vessel. The prosthesis has a distal end including barbs, a middle portion, and a proximal end including barbs. The prosthesis comprises a self-expanding stent and a graft covering disposed thereon.

When inserted into the body, the prosthesis is in the delivery configuration having a radially compressed distal end covered by a first and second sleeve, a radially compressed proximal end covered by a third and fourth sleeve, and a middle portion that is not covered by any sleeves. The middle portion may be expanded or it may be compressed or partially compressed by the physician's fingers or by forceps. The distal end of the prosthesis may be inserted into a vessel portion (107A or 107B) through an opening in the vessel by a sufficient distance to allow the barbs of the prosthesis to engage within the tissue of the vessel. In some embodiments, the vessel portion initially selected is the non-blood supplying vessel end. In one embodiment, the vessel portion (107B) may be manually pulled over the distal end of the prosthesis using a hand or forceps, for example. The first sleeve is located on the distal-most end of the prosthesis and the second sleeve is located proximally adjacent the first sleeve on the distal end of the prosthesis. The first sleeve comprises a thinner wall thickness than the second sleeve. An activating agent may then be applied to the first and second sleeves at the distal end of the prosthesis to begin dissolving the sleeves. Since the first sleeve has a thinner wall thickness than the second sleeve, it will dissolve first, thereby allowing the portion of the stent covered by the first sleeve to expand and the barbs to engage the inner vessel wall. After an additional few seconds, the second sleeve will dissolve, thereby allowing the portion of the stent covered by the second sleeve to expand.

The other vessel portion (107A) may then be pulled over the proximal end of the prosthesis. A third sleeve is located on the proximal-most end of the prosthesis and a fourth sleeve is located distally adjacent the third sleeve on the proximal end of the prosthesis. The third sleeve comprises a thinner wall thickness than the fourth sleeve. An activating agent may then be applied to the third and fourth sleeves at the proximal end of the prosthesis to begin dissolving the sleeves. Since the third sleeve has a thinner wall thickness than the fourth sleeve, it will dissolve first, thereby allowing the portion of the stent covered by the third sleeve to expand and the barbs to engage the inner vessel wall. After an additional few seconds, the fourth sleeve will dissolve, thereby allowing the portion of the stent covered by the fourth sleeve to expand.

FIG. 10B shows vessel ends (107A and 107B) connected by the graft (109) to achieve hemostasis.

In another embodiment, a method of deploying a prosthesis is disclosed, which is similar to the methods shown in FIGS. 6A-6E and 10A-10B. The prosthesis comprises a self-expanding stent and a graft covering disposed thereon. The prosthesis has a distal end including barbs, a middle portion, and a proximal end including barbs. The distal end may be radially compressed and a first sleeve may be disposed thereon to hold the distal end of the prosthesis in a radially compressed configuration. The proximal end may also be radially compressed and a second sleeve may be disposed thereon to hold the proximal end of the prosthesis in a radially compressed configuration. The middle portion of the prosthesis may be uncovered by the sleeves and thus, it may be in its radially expanded configuration or it may be compressed or partially compressed by a physician's hand or forceps, for example. The first sleeve comprises a thinner wall thickness at its distal end as compared to its proximal end. The second sleeve comprises a thinner wall thickness at its proximal end as compared to its distal end.

When a vessel is transected, it is split apart such that it includes a first end and a second end, which were initially joined together before the vessel was transected. The vessel may be accessed through an open surgical procedure and a clinician, such as a physician, can manually place the distal end of the prosthesis into a lumen of a first end of the transected vessel. An activating agent may then be applied to the distal end of the prosthesis to dissolve the sleeve disposed thereon. Since the first sleeve disposed on the distal end of the prosthesis comprises a thinner wall thickness at its distal end, the distal end of the first sleeve will dissolve first, thereby allowing the portion of the prosthesis covered by the thinner wall of the first sleeve to expand. The portion allowed to expand first comprises the barbs and accordingly, the barbs may engage the inner vessel wall. Subsequently, the remainder of the first sleeve, such as the portion comprising the thicker wall thickness, will dissolve, thereby allowing the portion of the prosthesis covered by the remainder of the sleeve to expand.

Next, a clinician can manually place the proximal end of the prosthesis into a lumen of a second end of the transected vessel. An activating agent may then be applied to the proximal end of the prosthesis to dissolve the sleeve disposed thereon. Since the second sleeve disposed on the proximal end of the prosthesis comprises a thinner wall thickness at its proximal end, the proximal end of the second sleeve will dissolve first, thereby allowing the portion of the prosthesis covered by the thinner wall of the second sleeve to expand. The portion allowed to expand first comprises the barbs and accordingly, the barbs may engage the inner vessel wall. Subsequently, the remainder of the second sleeve, such as the portion comprising the thicker wall thickness, will dissolve, thereby allowing the portion of the prosthesis covered by the remainder of the sleeve to expand.

With the barbs on the distal and proximal ends of the prosthesis engaged with the inner vessel walls, and the prosthesis being radially expanded, the vessel is in a repaired state and hemostasis is achieved.

Any of the foregoing procedures may also be used in connection with a prosthesis comprising a first sleeve having an additional sleeve overlapping an end of the first sleeve.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of open surgical repair of a lacerated or transected body vessel to obtain fluid stability while maintaining fluid flow through the body vessel, comprising:

inserting a distal end of a prosthesis into a first vessel portion of the body vessel, wherein the prosthesis comprises a self-expanding stent and a graft body, the distal end of the prosthesis being retained in a radially compressed configuration with a distal end sleeve comprising a section having a thinner wall thickness and a section having a thicker wall thickness, wherein the section having the thicker wall thickness is located proximally adjacent the section having the thinner wall thickness;

applying an activating agent to the distal end sleeve;

dissolving the distal end sleeve thereby allowing a distal end of the self-expanding stent to expand and engage the first vessel portion, the section having the thinner wall thickness dissolving at a rate which is faster than a rate of the section having the thicker wall thickness thereby allowing a distal-most end to expand and contact the vessel before the proximally adjacent portion;

inserting a proximal end of the prosthesis into a second vessel portion of the body vessel, the proximal end of the prosthesis being retained in a radially compressed configuration with a proximal end sleeve comprising a section having a thinner wall thickness and a section having a thicker wall thickness, wherein the section having the thicker wall thickness is located distally adjacent the section having the thinner wall thickness;

applying the activating agent to the proximal end sleeve; and dissolving the proximal end sleeve thereby allowing a proximal end of the self-expanding stent to expand and engage the second vessel portion, the section having the thinner wall thickness dissolving at a rate which is faster than a rate of the section having the thicker wall thickness thereby allowing a proximal-most end to expand and contact the vessel before the distally adjacent portion;

the prosthesis comprising a longitudinal length sufficient to bridge and seal the laceration or bridge and interconnect the gap between the transection.

2. The method of claim 1, wherein the section of the distal end sleeve having the thicker wall thickness comprises two or more overlapping sleeves.

3. The method of claim 1, wherein the section of the proximal end sleeve having the thicker wall thickness comprises two or more overlapping sleeves.

4. The method of claim 1, wherein the proximal end sleeve comprises a single sleeve and the distal end sleeve comprises a single sleeve.

5. The method of claim 1, wherein the distal and proximal ends of the prosthesis each comprise one or more barbs to engage tissue of the body vessel to fix the distal and proximal ends to the first and second vessel portions.

6. The method of claim 1, wherein the proximal end sleeve and the distal end sleeve comprise hydroxypropyl methylcellulose.

7. The method of claim 1, wherein the body vessel is transected, the prosthesis being inserted into the first and second vessel portions through the gap between the transected vessel portions.

8. The method of claim 1, wherein a ratio of a wall thickness of the section of the distal end sleeve having the thicker wall thickness to the section of the distal end sleeve having the thinner wall thickness is from about 1.2:1 to about 4:1, and a ratio of a wall thickness of the section of the proximal end sleeve having the thicker wall thickness to the section of the proximal end sleeve having the thinner wall thickness is from about 1.2:1 to about 4:1.

9. The method of claim 1, wherein the distal end of the prosthesis comprises one or more barbs covered by the section of the distal end sleeve having the thinner wall thickness and the proximal end of the prosthesis comprises one or more barbs covered by the section of the proximal end sleeve having the thinner wall thickness.

10. The method of claim 1, wherein the sections of the proximal end sleeve and the distal end sleeve having the thinner wall thicknesses dissolve in less than about 5 to about 10 seconds after the activating agent is applied and the sections of the proximal end sleeve and the distal end sleeve having the thicker wall thicknesses dissolve in about 8 to about 13 seconds after the activating agent is applied.

11. The method of claim 1, wherein the proximal end of the prosthesis comprises a first tube located proximally adjacent the proximal end sleeve and a first cap disposed around the first tube and the proximal end sleeve, wherein the distal end of the prosthesis comprises a second tube located distally adjacent the distal end sleeve and a second cap disposed around the second tube and the distal end sleeve, further comprising the steps of:
removing the second cap and the second tube before inserting the distal end of the prosthesis into the body vessel, and
removing the first cap and the first tube before inserting the proximal end of the prosthesis into the body vessel.

12. The method of claim 1, further comprising clamping the first and second vessel portions to restrict fluid flow prior to inserting the distal and proximal ends of the prosthesis.

13. The method of claim 1, wherein the activating agent is saline or blood.

14. The method of claim 1, wherein a first sleeve comprises the section of the distal end sleeve having the thinner wall thickness and a second sleeve comprises the section of the distal end sleeve having the thicker wall thickness.

15. The method of claim 14, wherein the first and second sleeves are placed in series at the distal end of the prosthesis along the longitudinal axis.

16. The method of claim 1, wherein a third sleeve comprises the section of the proximal end sleeve having the thinner wall thickness and a fourth sleeve comprises the section of the proximal end sleeve having the thicker wall thickness.

17. The method of claim 16, wherein the third and fourth sleeves are placed in series at the proximal end of the prosthesis along the longitudinal axis.

18. A prosthesis comprising:
a self-expanding stent having a distal end, a middle portion, and a proximal end, the distal and proximal ends comprising one or more barbs; and
a graft body;
wherein the distal end of the self-expanding stent comprises a radially compressed configuration and a distal end sleeve comprising a distal section having a thinner wall thickness and a proximal section having a thicker wall thickness, wherein the proximal section is located proximally adjacent to the distal section;
wherein the proximal end of the self-expanding stent comprises a radially compressed configuration and a proximal end sleeve comprising a proximal section having a thinner wall thickness and a distal section having a thicker wall thickness, wherein the proximal section having the thinner wall thickness is located proximally adjacent the distal section having the thicker wall thickness;
wherein the distal end sleeve and the proximal end sleeve are dissolvable, wherein the distal section of the proximal end sleeve is configured to dissolve at a rate which is slower than a rate of the proximal section of the proximal end sleeve, and wherein the proximal section of the distal end sleeve is configured to dissolve at a rate which is slower than a rate of the distal section of the distal end sleeve.

19. The prosthesis of claim 18, further comprising:
a first tube located distally adjacent the distal end sleeve;
a first cap disposed around the first tube and the distal end sleeve;
a second tube located proximally adjacent the proximal end sleeve; and
a second cap disposed around the second tube and the proximal end sleeve.

20. A prosthesis comprising:
a self-expanding stent having a first end, a middle portion, and a second end, the first end and second end each comprising a barb, and a graft body;
a first sleeve configured to retain the first end of the self-expanding stent in a radially compressed configuration, the first sleeve comprising an terminal portion and an adjacent portion wherein the adjacent portion is configured to be closer to the middle portion of the stent than the terminal portion, wherein the first sleeve is at least partially dissolvable, and wherein the terminal portion of the first sleeve is configured to dissolve at a faster rate than a rate of the adjacent portion of the first sleeve;
a second sleeve configured to retain the second end of the self-expanding stent in a radially compressed configuration, the second sleeve comprising an terminal portion and an adjacent portion wherein the adjacent portion is configured to be closer to the middle portion of the stent than the terminal portion, wherein the second sleeve is at least partially dissolvable, and wherein the terminal portion of the second sleeve is configured to dissolve at a faster rate than a rate of the adjacent portion of the second sleeve.

21. The prosthesis of claim 20, wherein the rate of dissolving of the terminal portions and adjacent portions of the first sleeve and the second sleeve is proportional to the thickness of the inner portions and outer portions, wherein the adjacent portion of the first sleeve is thicker than the terminal portion of the first sleeve, and wherein the adjacent portion of the second sleeve is thicker than the terminal portion of the second sleeve.

22. The prosthesis of claim 21, wherein the first sleeve comprises a first cannula extending along the adjacent portion and the terminal portion of the first sleeve, and a second cannula encircling the first cannula and extending only along the adjacent portion of the first sleeve.

* * * * *